United States Patent
Addis et al.

(10) Patent No.: US 12,018,062 B2
(45) Date of Patent: *Jun. 25, 2024

(54) T CELL RECEPTORS

(71) Applicant: Immunocore Limited, Abingdon (GB)

(72) Inventors: Philip William Addis, Abingdon (GB); Nicole Joy Bedke, Abingdon (GB); Lucie Bouard, Abingdon (GB); Stephen Harper, Abingdon (GB); Nathaniel Liddy, Abingdon (GB); Tara Mahon, Abingdon (GB); Ronan Pádraic O'Dwyer, Abingdon (GB)

(73) Assignee: Immunocore Limited, Abingdon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/324,425

(22) Filed: May 26, 2023

(65) Prior Publication Data
US 2023/0416335 A1  Dec. 28, 2023

Related U.S. Application Data

(63) Continuation of application No. 16/624,853, filed as application No. PCT/EP2018/066287 on Jun. 19, 2018, now Pat. No. 11,718,657.

(30) Foreign Application Priority Data
Jun. 20, 2017 (GB) .................. 1709866

(51) Int. Cl.
*C07K 14/725* (2006.01)
*A61K 35/17* (2015.01)
(Continued)

(52) U.S. Cl.
CPC .......... *C07K 14/7051* (2013.01); *A61K 35/17* (2013.01); *A61K 45/06* (2013.01);
(Continued)

(58) Field of Classification Search
CPC .......... C07K 14/7051; C07K 16/2809; A61K 35/17; A61K 45/06; A61K 47/6849; A61K 38/00; A61P 35/00
See application file for complete search history.

(56) References Cited

U.S. PATENT DOCUMENTS

| | | |
|---|---|---|
| 9,228,007 B1 | 1/2016 | Kitchen et al. |
| 11,427,624 B2 | 8/2022 | Addis et al. |

(Continued)

FOREIGN PATENT DOCUMENTS

| | | |
|---|---|---|
| WO | WO 1998/039482 A1 | 9/1998 |
| WO | WO 1999/018129 A1 | 4/1999 |

(Continued)

OTHER PUBLICATIONS

Kessler, J.H., et al (2001) Efficient Identification of Novel HLA-A*0201-presented cytotoxic T lymphocyte epitopes in the widely expressed tumor antigen PRAME by proteasome-mediated digestion analysis J. Exp. Med. 193(1); 73-88 (Year: 2001).*

(Continued)

*Primary Examiner* — Scarlett Y Goon
*Assistant Examiner* — Audrey L BUttice
(74) *Attorney, Agent, or Firm* — Fenwick & West LLP

(57) ABSTRACT

The present invention relates to T cell receptors (TCRs) that bind the HLA-A*02 restricted peptide SLLQHLIGL (SEQ ID NO: 1) derived from the germline cancer antigen PRAME. Said TCRs may comprise non-natural mutations within the alpha and/or beta variable domains relative to a native PRAME TCR. The TCRs of the invention are particularly suitable for use as novel immunotherapeutic reagents for the treatment of malignant disease.

22 Claims, 12 Drawing Sheets

Specification includes a Sequence Listing.

(51) Int. Cl.
  *A61K 38/00* (2006.01)
  *A61K 45/06* (2006.01)
  *A61K 47/68* (2017.01)
  *A61P 35/00* (2006.01)
  *C07K 16/28* (2006.01)

(52) U.S. Cl.
  CPC .......... *A61K 47/6849* (2017.08); *A61P 35/00* (2018.01); *C07K 16/2809* (2013.01); *A61K 38/00* (2013.01)

(56) References Cited

U.S. PATENT DOCUMENTS

| | | |
|---|---|---|
| 2012/0225481 A1 | 9/2012 | Jakobsen et al. |
| 2015/0191524 A1 | 7/2015 | Smith et al. |
| 2016/0199479 A1 | 7/2016 | Su et al. |
| 2017/0051036 A1 | 2/2017 | Jakobsen et al. |
| 2021/0371493 A1 | 12/2021 | Jakobsen et al. |
| 2022/0235113 A1 | 7/2022 | Jakobsen et al. |

FOREIGN PATENT DOCUMENTS

| | | | |
|---|---|---|---|
| WO | WO 2001/062908 A2 | 8/2001 | |
| WO | WO 2003/020763 A3 | 5/2003 | |
| WO | WO 2004/033685 A1 | 4/2004 | |
| WO | WO 2006/000830 A2 | 1/2006 | |
| WO | WO 2010/133828 A1 | 11/2010 | |
| WO | WO 2011/001152 A1 | 1/2011 | |
| WO | WO-2011001152 A1 * | 1/2011 | .......... C07K 14/705 |
| WO | WO 2014/018863 A1 | 1/2014 | |
| WO | WO 2015/022520 A1 | 2/2015 | |
| WO | WO 2015/136072 A1 | 9/2015 | |
| WO | WO 2016/142783 A2 | 9/2016 | |
| WO | WO 2016/170348 A3 | 10/2016 | |
| WO | WO 2018/067618 A1 | 4/2018 | |

OTHER PUBLICATIONS

Amir, A.L. et al., "PRAME-Specific Allo-HLA-Restricted T Cells with Potent Antitumor Reactivity Useful for Therapeutic T-Cell Receptor Gene Transfer," *Clinical Cancer Research*, Sep. 1, 2011, vol. 17, No. 17, p. 5615-5625.

Bragado et al., "Allelic polymorphism in the coding region of human TCR Cα gene and characterization of structural variability in the α chain constant domain," International Immunology, vol. 6, Issue 2, Feb. 1994, pp. 223-230.

Chailyan, A., et al., "The association of heavy and light chain variable domains in antibodies: implications for antigen specificity," *FEBS Journal*, vol. 278, Issue 16, Aug. 2011, pp. 2858-2866.

Chang, A. et al., "A therapeutic T cell receptor mimic antibody targets tumor-associated PRAME peptide/HLA-I antigens," *The Journal of Clinical Investigation*, Jul. 2017, vol. 127, No. 7, p. 2705-2718.

Davis, M. et al., "Ligand Recognition By αβ T Cell Receptors," *Annual Review of Immunology*, vol. 16, Apr. 1998, pp. 523-544.520.

Doolan et al., "Prevalence and prognostic and predictive relevance of PRAME in breast cancer," *Breast Cancer Research and Treatment*, vol. 109, pp. 359-365 (2008).

Epel et al., "A functional recombinant single-chain T cell receptor fragment capable of selectively targeting antigen-presenting cells," Cancer Immunology, Immunotherapy, Nov. 2002, 51(10):565-73.

Epping et al., "A Causal Role for the Human Tumor Antigen Preferentially Expressed Antigen of Melanoma in Cancer," *Cancer Research*, vol. 66, Issue 22, Nov. 15, 2006, pp. 10639-10642.

Ercolak et al., "PRAME Expression and It's Clinical Relevance in Hodgkin's Lymphoma," *Acta Haematologica*, vol. 134, No. 4, Nov. 2015, pp. 199-207.

Griffioen et al., "Detection and Functional Analysis of CD8+ T Cells Specific for PRAME: a Target for T-Cell Therapy," *Clinical Cancer Research*, May 15, 2006, vol. 12, Issue 10, pp. 3130-3136.

Hoo et al., "Characterization of a single-chain T-cell receptor expressed in *Escherichia coli*," *Proceedings of the National Academy of Sciences*, May 1999, vol. 89; Issue 10, pp. 4759-4763.

Ikeda et al., "Characterization of an Antigen That Is Recognized on a Melanoma Showing Partial HLA Loss by CTL Expressing an NK Inhibitory Receptor," *Immunity*, vol. 6, pp. 199-208, Feb. 1997.

International Search Report and Written Opinion, PCT Application No. PCT/EP2018/066287, dated Aug. 29, 2018, 14 pages.

Kessler et al., "Efficient Identification of Novel HLA-A*0201-Presented Cytotoxic T Lymphocyte Epitopes in the Widely Expressed Tumor Antigen Prame by Proteasome-Mediated Digestion Analysis," *Journal of Experimental Medicine*, Jan. 2, 2001, vol. 193, No. 1, pp. 73-88.

Knapp, B., et al. "Variable Regions of Antibodies and T-Cell Receptors May Not Be Sufficient in Molecular Simulations Investigating Binding," *Journal of Chemical Theory and Computation*, 13, 3097-3105 (Year: 2017).

Li, B. et al., "Landscape of tumor-infiltrating T cell repertoire of human cancers," *Nature Genetics*, May 30, 2016, vol. 48, p. 725-732.

Liddy, N. et al., " Monoclonal TCR-redirected tumor cell killing", *Nature Medicine*, May 6, 2012, vol. 18, No. 6, p. 980-987.

Løset, G.A., et al. "Phage display engineered T cell receptors as tools for the study of tumor peptide-MHC interactions," Frontiers in Oncology, Jan. 2015, vol. 4, Article 378, pp. 1-7.

Matsushita et al., "Preferentially expressed antigen of melanoma (PRAME) in the development of diagnostic and therapeutic methods for hematological malignancies," *Leukemia & Lymphoma*, vol. 44, Issue 3, 2003, pp. 439-444.

Mitsuhashi et al., "Prognostic significance of PRAME expression based on immunohistochemistry for diffuse large B-cell lymphoma patients treated with R-CHOP therapy," *International Journal of Hematology*, vol. 100, pp. 88-95 (2014).

Proto-Siqueira et al., "PRAME is a membrane and cytoplasmic protein aberrantly expressed in chronic lymphocytic leukemia and mantle cell lymphoma," *Leukemia Research*, vol. 30, Issue 11, Nov. 2006, pp. 1333-1339.

Quintarelli, C. et al., "High-avidity cytotoxic T lymphocytes specific for a new PRAME-derived peptide can target leukemic and leukemic-precursor cells," *Blood*, Mar. 24, 2011, vol. 117, No. 12, p. 3353-3362.

Rabia, L., et al., "Understanding and overcoming trade-offs between antibody affinity, specificity, stability, and solubility," *Biochemical Engineering Journal*, vol. 137, Sep. 15, 2018, pp. 365-374.

Rosenberg et al., "Adoptive cell transfer: a clinical path to effective cancer immunotherapy," *Nature Reviews Cancer*, Apr. 2008, 8(4):299-308.

Schodin, B. et al., "Binding properties and solubility of single-chain T cell receptors expressed in *E. coli*," *Molecular Immunology*, vol. 33, Issue 9, Jun. 1996, pp. 819-829.

Szczepanski et al., "PRAME expression in head and neck cancer correlates with markers of poor prognosis and might help in selecting candidates for retinoid chemoprevention in pre-malignant lesions," *Oral Oncology*, vol. 49, Issue 2, Feb. 2013, pp. 144-151.

Van Baren et al., "PRAME, a gene encoding an antigen recognized on a human melanoma by cytolytic T cells, is expressed in acute leukaemia cells," *British Journal of Haematology*, 1998, 102(5), pp. 1376-1379.

Walseng, E., et al., "Soluble T-cell Receptors Produced in Human Cells for Targeted Delivery," *PLOS ONE*, Apr. 2015, 10(4): e0119559; pp. 1-15.

Weidanz et al., "Display of functional αβ single-chain T-cell receptor molecules on the surface of bacteriophage," *Journal of Immunological Methods*, vol. 221, Issues 1-2, Dec. 1998, pp. 59-76.

Extended European Search Report, European Patent Office Application No. 22216195.2, dated Jul. 12, 2023, 13 pages.

Mccormack, E., et al., "Bi-specific TCR-anti CD3 redirected T-cell targeting of NY-ESO-1- and LAGE-1-positive tumors," *Cancer Immunology, Immunotherapy*, 62, 773-785 (2013). https://doi.org/10.1007/s00262-012-1384-4.

* cited by examiner

Figure 1

SEQ ID NO: 2 Amino acid sequence of the scaffold alpha chain extracellular region. CDRs are underlined. The extracellular constant region is shown in italics

```
            10         20         30         40         50         60
        DAKTTQPNSM ESNEEEPVHL PCNHSTISGT DYIHWYRQLP SQGPEYVIHG LTSNVNNRMA
            70         80         90        100        110        120
        SLAIAEDRKS STLILHRATL RDAAVYYCIL ILGHSGAGSY QLTFGKGTKL SVIPNIQNPD
           130        140        150        160        170        180
        PAVYQLRDSK SSDKSVCLFT DFDSQTNVSQ SKDSDVYITD KTVLDMRSMD FKSNSAVAWS
           190        200
        NKSDFACANA FNNSIIPEDT
```

SEQ ID NO: 3 Amino acid sequence of the scaffold beta chain extracellular region. CDRs are underlined. The extracellular constant region is shown in italics

```
            10         20         30         40         50         60
        DGGITQSPKY LFRKEGQNVT LSCEQNLNHD AMYWYRQDPG QGLRLIYYSQ IVNDFQKGDI
            70         80         90        100        110        120
        AEGYSVSREK KESFPLTVTS AQKNPTAFYL CASSPWTSGS REQYFGPGTR LTVTEDLKNV
           130        140        150        160        170        180
        FPPEVAVFEP SEAEISHTQK ATLVCLATGF YPDHVELSWW VNGKEVHSGV STDPQPLKEQ
           190        200        210        220        230        240
        PALNDSRYCL SSRLRVSATF WQNPRNHFRC QVQFYGLSEN DEWTQDRAKP VTQIVSAEAW

GRAD
```

Figure 2

SEQ ID NO: 4 Amino acid sequence of the soluble extracellular region of the scaffold TCR alpha chain. CDRs are underlined. The constant region is shown in italics and the non-native cysteine residue is shown in bold (at position 48 of constant region)

```
         10         20         30         40         50         60
DAKTTQPNSM ESNEEEPVHL PCNHSTISGT DYIHWYRQLP SQGPEYVIHG LTSNVNNRMA
         70         80         90        100        110        120
SLAIAEDRKS STLILHRATL RDAAVYYCIL ILGHSGAGSY QLTFGKGTKL SVIPNIQNPD
        130        140        150        160        170        180
PAVYQLRDSK SSDKSVCLFT DFDSQTNVSQ SKDSDVYITD KCVLDMRSMD FKSNSAVAWS
        190        200
NKSDFACANA FNNSIIPEDT
```

SEQ ID NO: 5 Amino acid sequence of the soluble extracellular region of the scaffold TCR beta chain The constant region is shown in italics and the non-native cysteine residue is shown in bold (at position 57 of constant region). Additional non-native amino acids at position 75 and position 89 of the constant region are also shown in bold.

```
         10         20         30         40         50         60
DGGITQSPKY LFRKEGQNVT LSCEQNLNHD AMYWYRQDPG QGLRLIYYSQ IVNDFQKGDI
         70         80         90        100        110        120
AEGYSVSREK KESFPLTVTS AQKNPTAFYL CASSPWTSGS REQYFGPGTR LTVTEDLKNV
        130        140        150        160        170        180
FPPEVAVFEP SEAEISHTQK ATLVCLATGF YPDHVELSWW VNGKEVHSGV CTDPQPLKEQ
        190        200        210        220        230        240
PALNDSRYAL SSRLRVSATF WQDPRNHFRC QVQFYGLSEN DEWTQDRAKP VTQIVSAEAW
GRAD
```

Figure 3

Amino acid sequences of mutated TCR alpha chain variable regions. CDRs are underlined and mutations are in bold

SEQ ID NO: 6 mutant alpha chain (a28)

G DAKTTQPNSM ESNEEEPVHL PCNHSTISGT DYIHWYRQLP SQGPEYVIHG LTSNVNNRMA SLAIAEDRKS STLILHRATL RDAAVYYCIL ILGHSRAGNY IATFGKGTKL SVIP

SEQ ID NO: 7 mutant alpha chain (a79)

G DAKTTQPNSM ESNEEEPVHL PCNHSTISGT DYIHWYRQLP SQGPEYVIHG LTSNVNNRMA SLAIAEDRKS STLILHRATL RDAAVYYCIL ILGHSRLGNY IATFGKGTKL SVIP

SEQ ID NO: 8 mutant alpha chain (a109)

G DAKTTQPNSM ESNEEEPVHL PCNHSTISGT DYIHWYRQLP SQGPEYVIHG LTSNVNNRMA SLAIAEDRKS STLILHRATL RDAAVYYCIL ILGHSRLGNY QATFGKGTKL SVIP

Figure 4

Amino acid sequences of mutated TCR beta chain variable regions. CDRs are underlined. Mutations are in bold

SEQ ID NO: 9 mutant beta chain (b50)
DGGITQSPKY LFRKEGQNVT LSCEQ<u>NLNHD AMY</u>WYRQDPG QGLRLIYY<u>SQ IMGDE</u>QKGDI
AEGYSVSREK KESFPLTVTS AQKNPTAFYL <u>CASSWWTGGA SPIS</u>FGPGTR LTVT

SEQ ID NO: 10 mutant beta chain (b57)
DGGITQSPKY LFRKEGQNVT LSCEQ<u>NLNHD AMY</u>WYRQDPG QGLRLIYY<u>SQ IMGDE</u>QKGDI
AEGYSVSREK KESFPLTVTS AQKNPTAFYL <u>CASSWWTSGA SPIS</u>FGPGTR LTVT

SEQ ID NO: 11 mutant beta chain (b46)
DGGITQSPKY LFRKEGQNVT LSCEQ<u>NLNHD AMY</u>WYRQDPG QGLRLIYY<u>SQ IMGDE</u>QKGDI
AEGYSVSREK KESFPLTVTS AQKNPTAFYL <u>CASSWWTGGS APIR</u>FGPGTR LTVT

SEQ ID NO: 12 mutant beta chain (b64)
DGGITQSPKY LFRKEGQNVT LSCEQ<u>NLNHD AMY</u>WYRQDPG QGLRLIYY<u>SQ IMNDE</u>QKGDI
AEGYSVSREK KESFPLTVTS AQKNPTAFYL <u>CASSWWTGGS APIR</u>FGPGTR LTVT

SEQ ID NO: 13 mutant beta chain (b67)
DGGITQSPKY LFRKEGQNVT LSCEQ<u>NLNHD AMY</u>WYRQDPG QGLRLIYY<u>SQ IMGDE</u>QKGDI
AEGYSVSREK KESFPLTVTS AQKNPTAFYL <u>CASSWWTSGS APIR</u>FGPGTR LTVT

SEQ ID NO: 14 mutant beta chain (b69)
DGGITQSPKY LFRKEGQNVT LSCEQ<u>NLNHD AMY</u>WYRQDPG QGLRLIYY<u>SQ IMGDE</u>QKGDI
AEGYSVSREK KESFPLTVTS AQKNPTAFYL <u>CASSWWTGGS AEIR</u>FGPGTR LTVT

SEQ ID NO: 15 mutant beta chain (b71)
DGGITQSPKY LFRKEGQNVT LSCEQ<u>NLNHD AMY</u>WYRQDPG QGLRLIYY<u>SQ IMGDE</u>QKGDI
AEGYSVSREK KESFPLTVTS AQKNPTAFYL <u>CASSWWTGGS APIY</u>FGPGTR LTVT

SEQ ID NO: 16 mutant beta chain (b73)
DGGITQSPKY LFRKEGQNVT LSCEQ<u>NLNHD AMY</u>WYRQDPG QGLRLIYY<u>SQ IMGDE</u>QKGDI
AEGYSVSREK KESFPLTVTS AQKNPTAFYL <u>CASSWWTGGA APIS</u>FGPGTR LTVT

Figure 4 cont'd

SEQ ID NO: 17 mutant beta chain (b74)
DGGITQSPKY LFRKEGQNVT LSCEQNLNHD AMYWYRQDPG QGLRLIYYSQ IMGDEQKGDI
AEGYSVSREK KESFPLTVTS AQKNPTAFYL CASSWWTGGA SPIRFGPGTR LTVT

SEQ ID NO: 18 mutant beta chain (b77)
DGGITQSPKY LFRKEGQNVT LSCEQNLNHD AMYWYRQDPG QGLRLIYYSQ IMGDEQKGDI
AEGYSVSREK KESFPLTVTS AQKNPTAFYL CASSWWTGGA APIRFGPGTR LTVT

SEQ ID NO: 19 mutant beta chain (b60)
DGGITQSPKY LFRKEGQNVT LSCEQNLNHD AMYWYRQDPG QGLRLIYYSQ IMGDEQKGDI
AEGYSVSREK KESFPLTVTS AQKNPTAFYL CASSWWTGGA SEISFGPGTR LTVT

SEQ ID NO: 20 mutant beta chain (b75)
DGGITQSPKY LFRKEGQNVT LSCEQNLNHD AMYWYRQDPG QGLRLIYYSQ IMGDEQKGDI
AEGYSVSREK KESFPLTVTS AQKNPTAFYL CASSWWTGGS APISFGPGTR LTVT

SEQ ID NO: 21 mutant beta chain (b58)
DGGITQSPKY LFRKEGQNVT LSCEQNLNHD AMYWYRQDPG QGLRLIYYSQ IMGDEQKGDI
AEGYSVSREK KESFPLTVTS AQKNPTAFYL CASSWWTGGS SPISFGPGTR LTVT

SEQ ID NO: 22 mutant beta chain (b63)
DGGITQSPKY LFRKEGQNVT LSCEQNLNHD AMYWYRQDPG QGLRLIYYSQ IVGDEQKGDI
AEGYSVSREK KESFPLTVTS AQKNPTAFYL CASSWWTGGS APIRFGPGTR LTVT

SEQ ID NO: 23 mutant beta chain (b66)
DGGITQSPKY LFRKEGQNVT LSCEQNLNHD AMYWYRQDPG QGLRLIYYSQ IMGDEQKGDI
AEGYSVSREK KESFPLTVTS AQKNPTAFYL CASSPWTGGS APIRFGPGTR LTVT

SEQ ID NO: 24 mutant beta chain (b76)
DGGITQSPKY LFRKEGQNVT LSCEQNLNHD AMYWYRQDPG QGLRLIYYSQ IMGDEQKGDI
AEGYSVSREK KESFPLTVTS AQKNPTAFYL CASSWWTGGS SPIRFGPGTR LTVT

Figure 5

Amino acid sequences of ImmTAC molecules (TCR-anti-CD3 fusions) comprising mutated TCR alpha and beta variable domains

ImmTAC1

SEQ ID NO: 25 alpha chain (a28)

G DAKTTQPNSM ESNEEEPVHL PCNHSTISGT DYIHWYRQLP SQGPEYVIHG LTSNVNNRMA
SLAIAEDRKS STLILHRATL RDAAVYYCIL ILGHSRAGNY IATFGKGTKL SVIPNIQNPD
PAVYQLRDSK SSDKSVCLFT DFDSQTNVSQ SKDSDVYITD KCVLDMRSMD FKSNSAVAWS
NKSDFACANA FNNSIIPEDT

SEQ ID NO: 26 beta chain (b50)

AIQMTQSPSS LSASVGDRVT ITCRASQDIR NYLNWYQQKP GKAPKLLIYY TSRLESGVPS
RFSGSGSGTD YTLTISSLQP EDFATYYCQQ GNTLPWTFGQ GTKVEIKGGG GSGGGGSGGG
GSGGGGSGGG SEVQLVESGG GLVQPGGSLR LSCAASGYSF TGYTMNWVRQ APGKGLEWVA
LINPYKGVST YNQKFKDRFT ISVDKSKNTA YLQMNSLRAE DTAVYYCARS GYYGDSDWYF
DVWGQGTLVT VSSGGGGSDG GITQSPKYLF RKEGQNVTLS CEQNLNHDAM YWYRQDPGQG
LRLIYYSQIM GDEQKGDIAE GYSVSREKKE SFPLTVTSAQ KNPTAFYLCA SSWWTGGASP
ISFGPGTRLT VTEDLKNVFP PEVAVFEPSE AEISHTQKAT LVCLATGFYP DHVELSWWVN
GKEVHSGVCT DPQPLKEQPA LNDSRYALSS RLRVSATFWQ DPRNHFRCQV QFYGLSENDE
WTQDRAKPVT QIVSAEAWGR AD

ImmTAC2

SEQ ID NO: 27 alpha chain (a79)

G DAKTTQPNSM ESNEEEPVHL PCNHSTISGT DYIHWYRQLP SQGPEYVIHG LTSNVNNRMA
SLAIAEDRKS STLILHRATL RDAAVYYCIL ILGHSRLGNY IATFGKGTKL SVIPNIQNPD
PAVYQLRDSK SSDKSVCLFT DFDSQTNVSQ SKDSDVYITD KCVLDMRSMD FKSNSAVAWS
NKSDFACANA FNNSIIPEDT

SEQ ID NO: 28 beta chain (b74)

AIQMTQSPSS LSASVGDRVT ITCRASQDIR NYLNWYQQKP GKAPKLLIYY TSRLESGVPS
RFSGSGSGTD YTLTISSLQP EDFATYYCQQ GNTLPWTFGQ GTKVEIKGGG GSGGGGSGGG
GSGGGGSGGG SEVQLVESGG GLVQPGGSLR LSCAASGYSF TGYTMNWVRQ APGKGLEWVA
LINPYKGVST YNQKFKDRFT ISVDKSKNTA YLQMNSLRAE DTAVYYCARS GYYGDSDWYF
DVWGQGTLVT VSSGGGGSDG GITQSPKYLF RKEGQNVTLS CEQNLNHDAM YWYRQDPGQG
LRLIYYSQIM GDEQKGDIAE GYSVSREKKE SFPLTVTSAQ KNPTAFYLCA SSWWTGGASP
IRFGPGTRLT VTEDLKNVFP PEVAVFEPSE AEISHTQKAT LVCLATGFYP DHVELSWWVN
GKEVHSGVCT DPQPLKEQPA LNDSRYALSS RLRVSATFWQ DPRNHFRCQV QFYGLSENDE
WTQDRAKPVT QIVSAEAWGR AD

Figure 5 cont'd

ImmTAC3

SEQ ID NO: 29 alpha chain (a79)

G DAKTTQPNSM ESNEEEPVHL PCNHSTISGT DYIHWYRQLP SQGPEYVIHG LTSNVNNRMA
SLAIAEDRKS STLILHRATL RDAAVYYCIL ILGHSRLGNY IATFGKGTKL SVIPNIQNPD
PAVYQLRDSK SSDKSVCLFT DFDSQTNVSQ SKDSDVYITD KCVLDMRSMD FKSNSAVAWS
NKSDFACANA FNNSIIPEDT

SEQ ID NO: 30 beta chain (b46)

AIQMTQSPSS LSASVGDRVT ITCRASQDIR NYLNWYQQKP GKAPKLLIYY TSRLESGVPS
RFSGSGSGTD YTLTISSLQP EDFATYYCQQ GNTLPWTFGQ GTKVEIKGGG GSGGGGSGGG
GSGGGGSGGG SEVQLVESGG GLVQPGGSLR LSCAASGYSF TGYTMNWVRQ APGKGLEWVA
LINPYKGVST YNQKFKDRFT ISVDKSKNTA YLQMNSLRAE DTAVYYCARS GYYGDSDWYF
DVWGQGTLVT VSSGGGGSDG GITQSPKYLF RKEGQNVTLS CEQNLNHDAM YWYRQDPGQG
LRLIYYSQIM GDEQKGDIAE GYSVSREKKE SFPLTVTSAQ KNPTAFYLCA SSWWTGGSAP
IRFGPGTRLT VTEDLKNVFP PEVAVFEPSE AEISHTQKAT LVCLATGFYP DHVELSWWVN
GKEVHSGVCT DPQPLKEQPA LNDSRYALSS RLRVSATFWQ DPRNHFRCQV QFYGLSENDE
WTQDRAKPVT QIVSAEAWGR AD

Figure 7
Cellular data demonstrating specificity of ImmTAC molecules comprising mutated TCR variable domains
a)
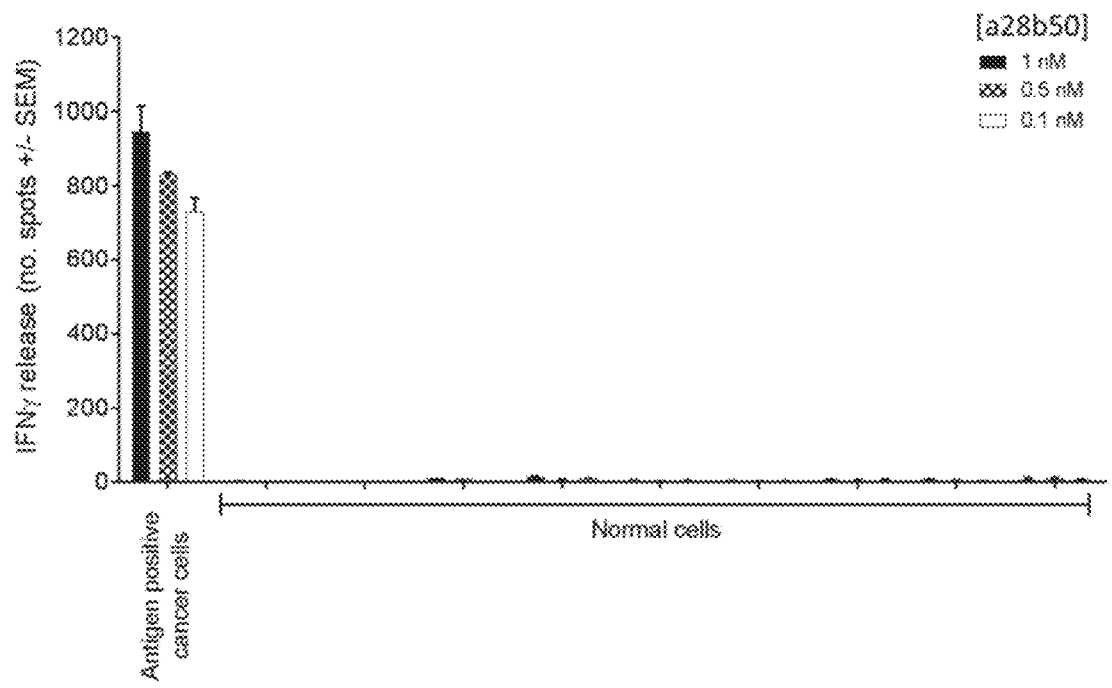
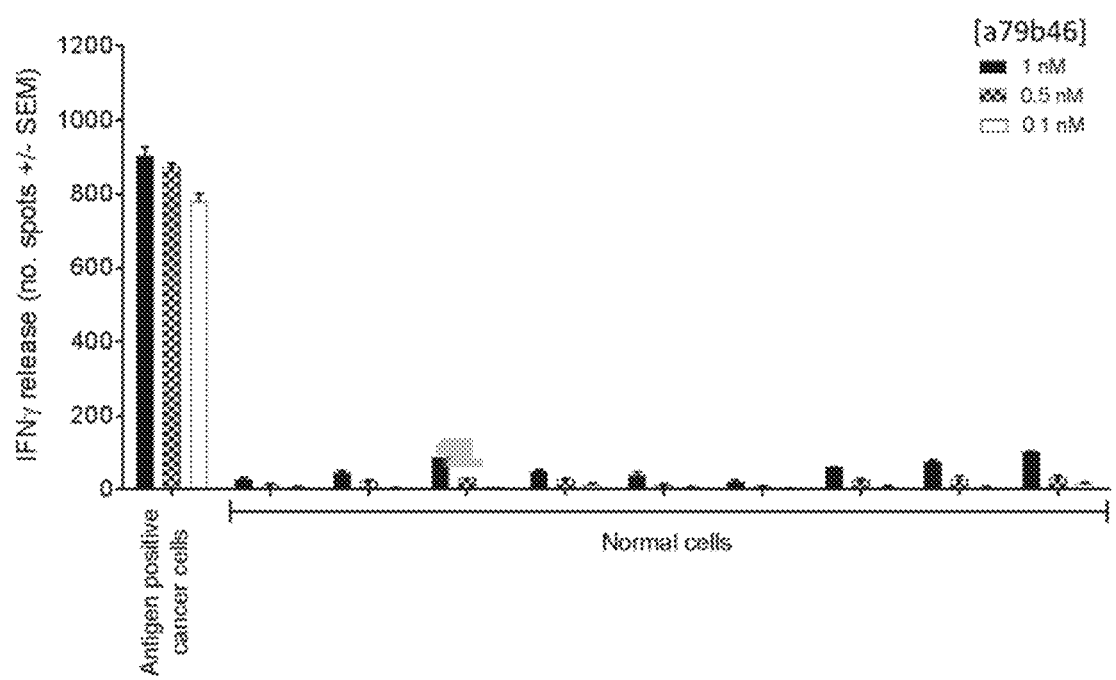

Figure 8
Cellular data demonstrating killing of cancer cells by ImmTAC molecules comprising mutated TCR variable domains
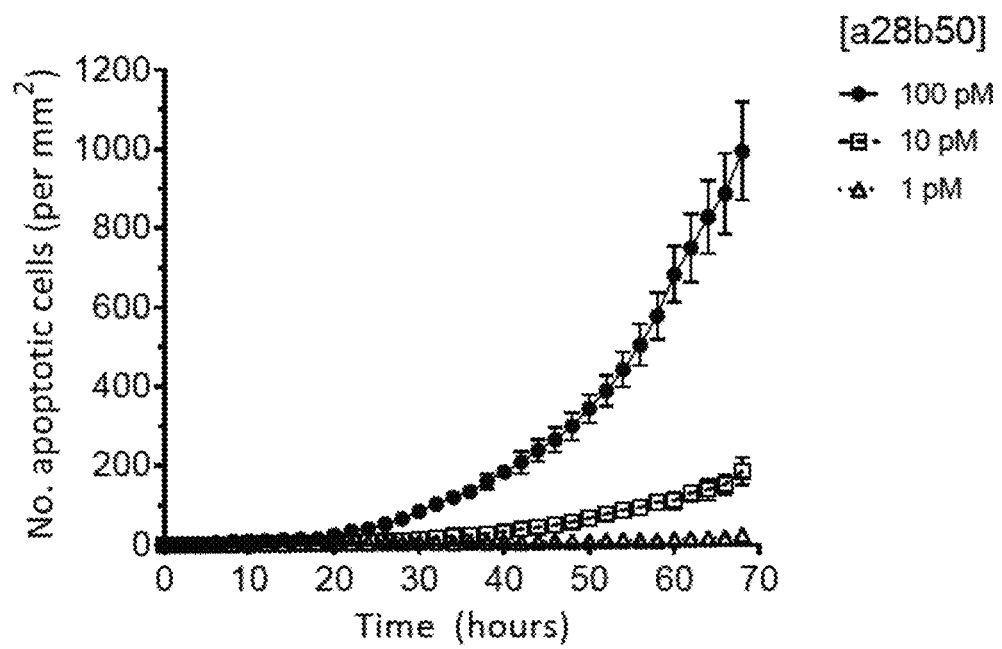
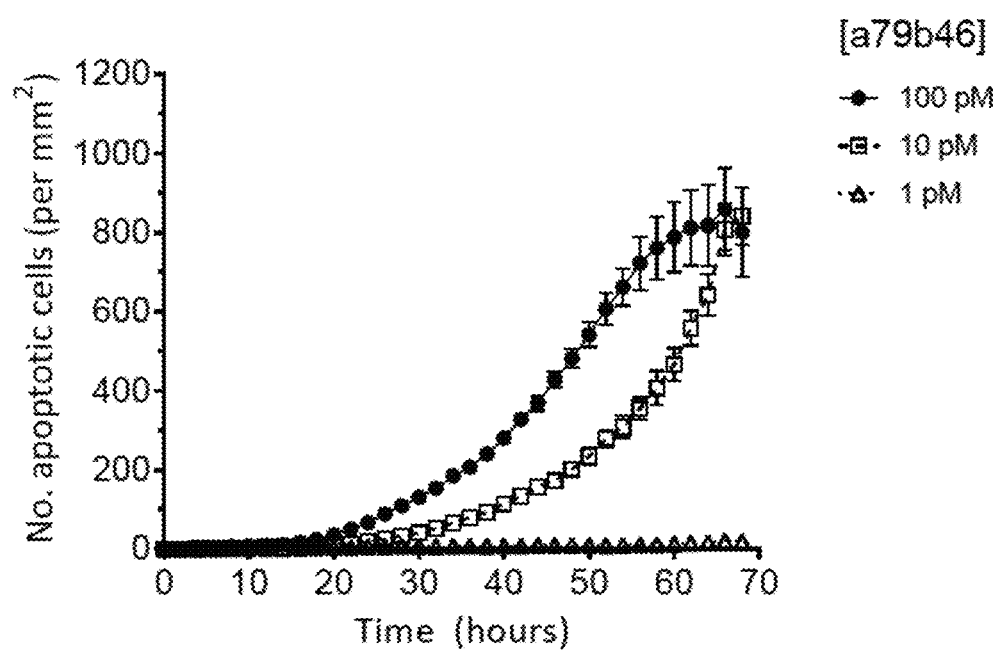

Figure 9
Further cellular data demonstrating killing of cancer cells by ImmTAC molecules comprising mutated TCR variable domains
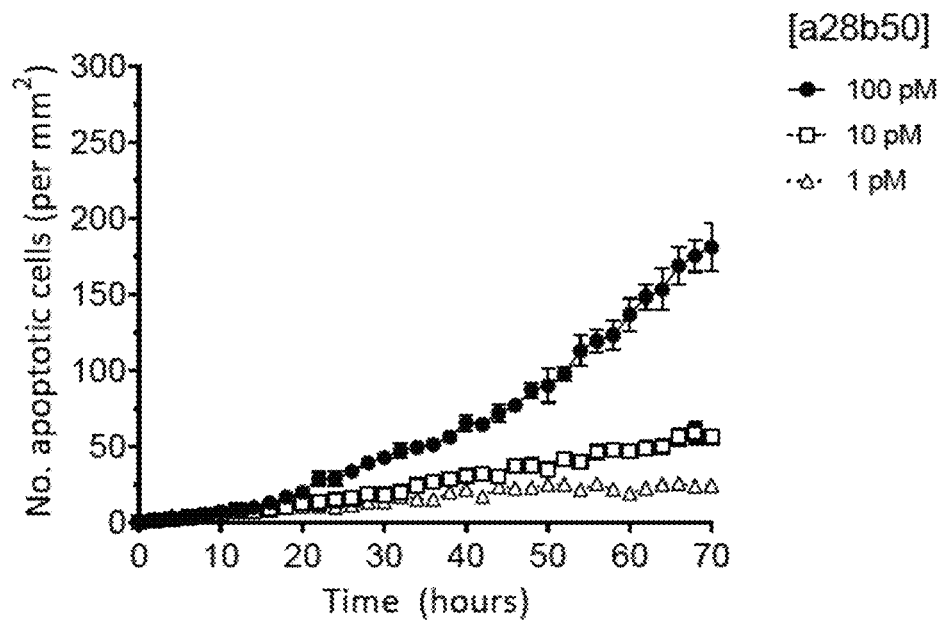
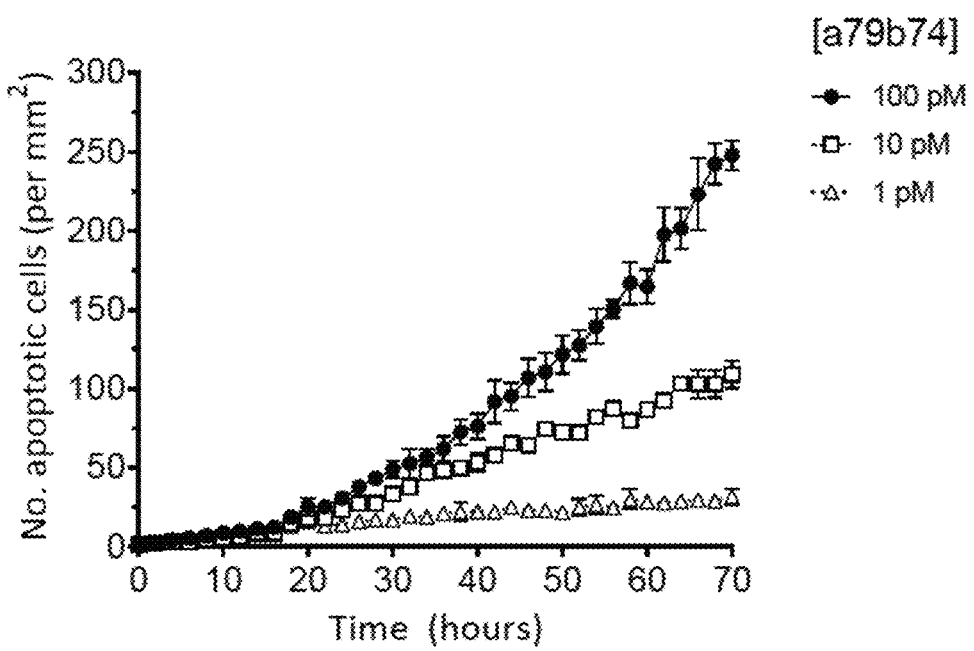

```
                             SEQUENCE LISTING

Sequence total quantity: 64
  SEQ ID NO: 1             moltype = AA  length = 9
  FEATURE                  Location/Qualifiers
  source                   1..9
                           mol_type = protein
                           organism = Homo sapiens
  SEQUENCE: 1
  SLLQHLIGL                                                                  9

SEQ ID NO: 2             moltype = AA  length = 200
  FEATURE                  Location/Qualifiers
  source                   1..200
                           mol_type = protein
                           organism = Homo sapiens
  SEQUENCE: 2
  DAKTTQPNSM ESNEEEPVHL PCNHSTISGT DYIHWYRQLP SQGPEYVIHG LTSNVNNRMA   60
  SLAIAEDRKS STLILHRATL RDAAVYYCIL ILGHSGAGSY QLTFGKGTKL SVIPNIQNPD  120
  PAVYQLRDSK SSDKSVCLFT DFDSQTNVSQ SKDSDVYITD KTVLDMRSMD FKSNSAVAWS  180
  NKSDFACANA FNNSIIPEDT                                              200

SEQ ID NO: 3             moltype = AA  length = 244
  FEATURE                  Location/Qualifiers
  source                   1..244
                           mol_type = protein
                           organism = Homo sapiens
  SEQUENCE: 3
  DGGITQSPKY LFRKEGQNVT LSCEQNLNHD AMYWYRQDPG QGLRLIYYSQ IVNDFQKGDI   60
  AEGYSVSREK KESFPLTVTS AQKNPTAFYL CASSPWTSGS REQYFGPGTR LTVTEDLKNV  120
  FPPEVAVFEP SEAEISHTQK ATLVCLATGF YPDHVELSWW VNGKEVHSGV STDPQPLKEQ  180
  PALNDSRYCL SSRLRVSATF WQNPRNHFRC QVQFYGLSEN DEWTQDRAKP VTQIVSAEAW  240
  GRAD                                                               244

SEQ ID NO: 4             moltype = AA  length = 200
  FEATURE                  Location/Qualifiers
  source                   1..200
                           mol_type = protein
                           organism = Homo sapiens
  SEQUENCE: 4
  DAKTTQPNSM ESNEEEPVHL PCNHSTISGT DYIHWYRQLP SQGPEYVIHG LTSNVNNRMA   60
  SLAIAEDRKS STLILHRATL RDAAVYYCIL ILGHSGAGSY QLTFGKGTKL SVIPNIQNPD  120
  PAVYQLRDSK SSDKSVCLFT DFDSQTNVSQ SKDSDVYITD KCVLDMRSMD FKSNSAVAWS  180
  NKSDFACANA FNNSIIPEDT                                              200

SEQ ID NO: 5             moltype = AA  length = 244
  FEATURE                  Location/Qualifiers
  source                   1..244
                           mol_type = protein
                           organism = Homo sapiens
  SEQUENCE: 5
  DGGITQSPKY LFRKEGQNVT LSCEQNLNHD AMYWYRQDPG QGLRLIYYSQ IVNDFQKGDI   60
  AEGYSVSREK KESFPLTVTS AQKNPTAFYL CASSPWTSGS REQYFGPGTR LTVTEDLKNV  120
  FPPEVAVFEP SEAEISHTQK ATLVCLATGF YPDHVELSWW VNGKEVHSGV CTDPQPLKEQ  180
  PALNDSRYAL SSRLRVSATF WQDPRNHFRC QVQFYGLSEN DEWTQDRAKP VTQIVSAEAW  240
  GRAD                                                               244
```

-continued

```
SEQ ID NO: 6              moltype = AA   length = 115
FEATURE                   Location/Qualifiers
source                    1..115
                          mol_type = protein
                          organism = Homo sapiens
SEQUENCE: 6
GDAKTTQPNS MESNEEEPVH LPCNHSTISG TDYIHWYRQL PSQGPEYVIH GLTSNVNNRM    60
ASLAIAEDRK SSTLILHRAT LRDAAVYYCI LILGHSRAGN YIATFGKGTK LSVIP        115

SEQ ID NO: 7              moltype = AA   length = 115
FEATURE                   Location/Qualifiers
source                    1..115
                          mol_type = protein
                          organism = Homo sapiens
SEQUENCE: 7
GDAKTTQPNS MESNEEEPVH LPCNHSTISG TDYIHWYRQL PSQGPEYVIH GLTSNVNNRM    60
ASLAIAEDRK SSTLILHRAT LRDAAVYYCI LILGHSRLGN YIATFGKGTK LSVIP        115

SEQ ID NO: 8              moltype = AA   length = 115
FEATURE                   Location/Qualifiers
source                    1..115
                          mol_type = protein
                          organism = Homo sapiens
SEQUENCE: 8
GDAKTTQPNS MESNEEEPVH LPCNHSTISG TDYIHWYRQL PSQGPEYVIH GLTSNVNNRM    60
ASLAIAEDRK SSTLILHRAT LRDAAVYYCI LILGHSRLGN YQATFGKGTK LSVIP        115

SEQ ID NO: 9              moltype = AA   length = 114
FEATURE                   Location/Qualifiers
source                    1..114
                          mol_type = protein
                          organism = Homo sapiens
SEQUENCE: 9
DGGITQSPKY LFRKEGQNVT LSCEQNLNHD AMYWYRQDPG QGLRLIYYSQ IMGDEQKGDI    60
AEGYSVSREK KESFPLTVTS AQKNPTAFYL CASSWWTGGA SPISFGPGTR LTVT         114

SEQ ID NO: 10             moltype = AA   length = 114
FEATURE                   Location/Qualifiers
source                    1..114
                          mol_type = protein
                          organism = Homo sapiens
SEQUENCE: 10
DGGITQSPKY LFRKEGQNVT LSCEQNLNHD AMYWYRQDPG QGLRLIYYSQ IMGDEQKGDI    60
AEGYSVSREK KESFPLTVTS AQKNPTAFYL CASSWWTSGA SPISFGPGTR LTVT         114

SEQ ID NO: 11             moltype = AA   length = 114
FEATURE                   Location/Qualifiers
source                    1..114
                          mol_type = protein
                          organism = Homo sapiens
SEQUENCE: 11
DGGITQSPKY LFRKEGQNVT LSCEQNLNHD AMYWYRQDPG QGLRLIYYSQ IMGDEQKGDI    60
AEGYSVSREK KESFPLTVTS AQKNPTAFYL CASSWWTGGS APIRFGPGTR LTVT         114

SEQ ID NO: 12             moltype = AA   length = 114
FEATURE                   Location/Qualifiers
source                    1..114
                          mol_type = protein
                          organism = Homo sapiens
SEQUENCE: 12
DGGITQSPKY LFRKEGQNVT LSCEQNLNHD AMYWYRQDPG QGLRLIYYSQ IMNDEQKGDI    60
AEGYSVSREK KESFPLTVTS AQKNPTAFYL CASSWWTGGS APIRFGPGTR LTVT         114

SEQ ID NO: 13             moltype = AA   length = 114
FEATURE                   Location/Qualifiers
source                    1..114
                          mol_type = protein
                          organism = Homo sapiens
SEQUENCE: 13
DGGITQSPKY LFRKEGQNVT LSCEQNLNHD AMYWYRQDPG QGLRLIYYSQ IMGDEQKGDI    60
AEGYSVSREK KESFPLTVTS AQKNPTAFYL CASSWWTSGS APIRFGPGTR LTVT         114

SEQ ID NO: 14             moltype = AA   length = 114
FEATURE                   Location/Qualifiers
source                    1..114
                          mol_type = protein
                          organism = Homo sapiens
SEQUENCE: 14
DGGITQSPKY LFRKEGQNVT LSCEQNLNHD AMYWYRQDPG QGLRLIYYSQ IMGDEQKGDI    60
```

```
AEGYSVSREK KESFPLTVTS AQKNPTAFYL CASSWWTGGS AEIRFGPGTR LTVT              114

SEQ ID NO: 15           moltype = AA  length = 114
FEATURE                 Location/Qualifiers
source                  1..114
                        mol_type = protein
                        organism = Homo sapiens
SEQUENCE: 15
DGGITQSPKY LFRKEGQNVT LSCEQNLNHD AMYWYRQDPG QGLRLIYYSQ IMGDEQKGDI        60
AEGYSVSREK KESFPLTVTS AQKNPTAFYL CASSWWTGGS APIYFGPGTR LTVT             114

SEQ ID NO: 16           moltype = AA  length = 114
FEATURE                 Location/Qualifiers
source                  1..114
                        mol_type = protein
                        organism = Homo sapiens
SEQUENCE: 16
DGGITQSPKY LFRKEGQNVT LSCEQNLNHD AMYWYRQDPG QGLRLIYYSQ IMGDEQKGDI        60
AEGYSVSREK KESFPLTVTS AQKNPTAFYL CASSWWTGGA APISFGPGTR LTVT             114

SEQ ID NO: 17           moltype = AA  length = 114
FEATURE                 Location/Qualifiers
source                  1..114
                        mol_type = protein
                        organism = Homo sapiens
SEQUENCE: 17
DGGITQSPKY LFRKEGQNVT LSCEQNLNHD AMYWYRQDPG QGLRLIYYSQ IMGDEQKGDI        60
AEGYSVSREK KESFPLTVTS AQKNPTAFYL CASSWWTGGA SPIRFGPGTR LTVT             114

SEQ ID NO: 18           moltype = AA  length = 114
FEATURE                 Location/Qualifiers
source                  1..114
                        mol_type = protein
                        organism = Homo sapiens
SEQUENCE: 18
DGGITQSPKY LFRKEGQNVT LSCEQNLNHD AMYWYRQDPG QGLRLIYYSQ IMGDEQKGDI        60
AEGYSVSREK KESFPLTVTS AQKNPTAFYL CASSWWTGGA APIRFGPGTR LTVT             114

SEQ ID NO: 19           moltype = AA  length = 114
FEATURE                 Location/Qualifiers
source                  1..114
                        mol_type = protein
                        organism = Homo sapiens
SEQUENCE: 19
DGGITQSPKY LFRKEGQNVT LSCEQNLNHD AMYWYRQDPG QGLRLIYYSQ IMGDEQKGDI        60
AEGYSVSREK KESFPLTVTS AQKNPTAFYL CASSWWTGGA SEISFGPGTR LTVT             114

SEQ ID NO: 20           moltype = AA  length = 114
FEATURE                 Location/Qualifiers
source                  1..114
                        mol_type = protein
                        organism = Homo sapiens
SEQUENCE: 20
DGGITQSPKY LFRKEGQNVT LSCEQNLNHD AMYWYRQDPG QGLRLIYYSQ IMGDEQKGDI        60
AEGYSVSREK KESFPLTVTS AQKNPTAFYL CASSWWTGGS APISFGPGTR LTVT             114

SEQ ID NO: 21           moltype = AA  length = 114
FEATURE                 Location/Qualifiers
source                  1..114
                        mol_type = protein
                        organism = Homo sapiens
SEQUENCE: 21
DGGITQSPKY LFRKEGQNVT LSCEQNLNHD AMYWYRQDPG QGLRLIYYSQ IMGDEQKGDI        60
AEGYSVSREK KESFPLTVTS AQKNPTAFYL CASSWWTGGS SPISFGPGTR LTVT             114

SEQ ID NO: 22           moltype = AA  length = 114
FEATURE                 Location/Qualifiers
source                  1..114
                        mol_type = protein
                        organism = Homo sapiens
SEQUENCE: 22
DGGITQSPKY LFRKEGQNVT LSCEQNLNHD AMYWYRQDPG QGLRLIYYSQ IVGDEQKGDI        60
AEGYSVSREK KESFPLTVTS AQKNPTAFYL CASSWWTGGS APIRFGPGTR LTVT             114

SEQ ID NO: 23           moltype = AA  length = 114
FEATURE                 Location/Qualifiers
source                  1..114
                        mol_type = protein
                        organism = Homo sapiens
```

```
SEQUENCE: 23
DGGITQSPKY LFRKEGQNVT LSCEQNLNHD AMYWYRQDPG QGLRLIYYSQ IMGDEQKGDI    60
AEGYSVSREK KESFPLTVTS AQKNPTAFYL CASSPWTGGS APIRFGPGTR LTVT         114

SEQ ID NO: 24           moltype = AA   length = 114
FEATURE                 Location/Qualifiers
source                  1..114
                        mol_type = protein
                        organism = Homo sapiens
SEQUENCE: 24
DGGITQSPKY LFRKEGQNVT LSCEQNLNHD AMYWYRQDPG QGLRLIYYSQ IMGDEQKGDI    60
AEGYSVSREK KESFPLTVTS AQKNPTAFYL CASSWWTGGS SPIRFGPGTR LTVT         114

SEQ ID NO: 25           moltype = AA   length = 201
FEATURE                 Location/Qualifiers
source                  1..201
                        mol_type = protein
                        organism = Homo sapiens
SEQUENCE: 25
GDAKTTQPNS MESNEEEPVH LPCNHSTISG TDYIHWYRQL PSQGPEYVIH GLTSNVNNRM    60
ASLAIAEDRK SSTLILHRAT LRDAAVYYCI LILGHSRAGN YIATFGKGTK LSVIPNIQNP   120
DPAVYQLRDS KSSDKSVCLF TDFDSQTNVS QSKDSDVYIT DKCVLDMRSM DFKSNSAVAW   180
SNKSDFACAN AFNNSIIPED T                                             201

SEQ ID NO: 26           moltype = AA   length = 502
FEATURE                 Location/Qualifiers
source                  1..502
                        mol_type = protein
                        organism = Homo sapiens
SEQUENCE: 26
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYTMNWVRQ APGKGLEWVA   180
LINPYKGVST YNQKFKDRFT ISVDKSKNTA YLQMNSLRAE GYYYCARS GYYGDSDWYF   240
DVWGQGTLVT VSSGGGGSDG GITQSPKYLF RKEGQNVTLS CEQNLNHDAM YWYRQDPGQG   300
LRLIYYSQIM GDEQKGDIAE GYSVSREKKE SFPLTVTSAQ KNPTAFYLCA SSWWTGGASP   360
ISFGPGTRLT VTEDLKNVFP PEVAVFEPSE AEISHTQKAT LVCLATGFYP DHVELSWWVN   420
GKEVHSGVCT DPQPLKEQPA LNDSRYALSS RLRVSATFWQ DPRNHFRCQV QFYGLSENDE   480
WTQDRAKPVT QIVSAEAWGR AD                                            502

SEQ ID NO: 27           moltype = AA   length = 201
FEATURE                 Location/Qualifiers
source                  1..201
                        mol_type = protein
                        organism = Homo sapiens
SEQUENCE: 27
GDAKTTQPNS MESNEEEPVH LPCNHSTISG TDYIHWYRQL PSQGPEYVIH GLTSNVNNRM    60
ASLAIAEDRK SSTLILHRAT LRDAAVYYCI LILGHSRLGN YIATFGKGTK LSVIPNIQNP   120
DPAVYQLRDS KSSDKSVCLF TDFDSQTNVS QSKDSDVYIT DKCVLDMRSM DFKSNSAVAW   180
SNKSDFACAN AFNNSIIPED T                                             201

SEQ ID NO: 28           moltype = AA   length = 502
FEATURE                 Location/Qualifiers
source                  1..502
                        mol_type = protein
                        organism = Homo sapiens
SEQUENCE: 28
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYTMNWVRQ APGKGLEWVA   180
LINPYKGVST YNQKFKDRFT ISVDKSKNTA YLQMNSLRAE DTAVYYCARS GYYGDSDWYF   240
DVWGQGTLVT VSSGGGGSDG GITQSPKYLF RKEGQNVTLS CEQNLNHDAM YWYRQDPGQG   300
LRLIYYSQIM GDEQKGDIAE GYSVSREKKE SFPLTVTSAQ KNPTAFYLCA SSWWTGGASP   360
IRFGPGTRLT VTEDLKNVFP PEVAVFEPSE AEISHTQKAT LVCLATGFYP DHVELSWWVN   420
GKEVHSGVCT DPQPLKEQPA LNDSRYALSS RLRVSATFWQ DPRNHFRCQV QFYGLSENDE   480
WTQDRAKPVT QIVSAEAWGR AD                                            502

SEQ ID NO: 29           moltype = AA   length = 201
FEATURE                 Location/Qualifiers
source                  1..201
                        mol_type = protein
                        organism = Homo sapiens
SEQUENCE: 29
GDAKTTQPNS MESNEEEPVH LPCNHSTISG TDYIHWYRQL PSQGPEYVIH GLTSNVNNRM    60
ASLAIAEDRK SSTLILHRAT LRDAAVYYCI LILGHSRLGN YIATFGKGTK LSVIPNIQNP   120
DPAVYQLRDS KSSDKSVCLF TDFDSQTNVS QSKDSDVYIT DKCVLDMRSM DFKSNSAVAW   180
SNKSDFACAN AFNNSIIPED T                                             201

SEQ ID NO: 30           moltype = AA   length = 501
```

| FEATURE | Location/Qualifiers |
|---|---|
| source | 1..501<br>mol_type = protein<br>organism = Homo sapiens |

SEQUENCE: 30
```
AIQMTQSPSS LSASVGDRVT ITCRASQDIR NYLNWYQQKP GKAPKLLIYY TSRLESGVPS   60
RFSGSGSGTD YTLTISSLQP EDFATYYCQQ GNTLPWTFGQ GTKVEIKGGG GSGGGGSGGG  120
GSGGGGSGGG SEVQLVESGG GLVQPGGSLR LSCAASGYSF TGYTMNWVRQ APGKGLEWVA  180
LINPYKGVST YNQKFKDRFT ISVDKSKNTA YLQMNSLRAE DTAVYYCARS GYYGDSDWYF  240
DVWGQGTLVT VSSGGGGSDG GITQSPKYLF RKEGQNVTLS CEQNLNHDAM YWYRQDPGQG  300
LRLIYYSQIM GDEQKGDIAE GYSVSREKKE SFPLTVTSAQ KNPTAFYLCA SSWWTGGSAP  360
IRFGPGTRLT VTEDLKNVFP PEVAVFEPSE AEISHTQKAT LVCLATGFYP DHVELSWWVN  420
GKEVHSGVCT DPQPLKEQPA LNDSRYALSS RLRVSATFWQ DPRNHFRCQV QFYGLSENDE  480
WTQDRAKPVT QIVSAEAWGR A                                           501
```

| SEQ ID NO: 31 | moltype = AA   length = 5 |
|---|---|
| FEATURE | Location/Qualifiers |
| source | 1..5<br>mol_type = protein<br>organism = Homo sapiens |

SEQUENCE: 31
GGGGS 5

| SEQ ID NO: 32 | moltype = AA   length = 5 |
|---|---|
| FEATURE | Location/Qualifiers |
| source | 1..5<br>mol_type = protein<br>organism = Homo sapiens |

SEQUENCE: 32
GGGSG 5

| SEQ ID NO: 33 | moltype = AA   length = 5 |
|---|---|
| FEATURE | Location/Qualifiers |
| source | 1..5<br>mol_type = protein<br>organism = Homo sapiens |

SEQUENCE: 33
GGSGG 5

| SEQ ID NO: 34 | moltype = AA   length = 5 |
|---|---|
| FEATURE | Location/Qualifiers |
| source | 1..5<br>mol_type = protein<br>organism = Homo sapiens |

SEQUENCE: 34
GSGGG 5

| SEQ ID NO: 35 | moltype = AA   length = 6 |
|---|---|
| FEATURE | Location/Qualifiers |
| source | 1..6<br>mol_type = protein<br>organism = Homo sapiens |

SEQUENCE: 35
GSGGGP 6

| SEQ ID NO: 36 | moltype = AA   length = 5 |
|---|---|
| FEATURE | Location/Qualifiers |
| source | 1..5<br>mol_type = protein<br>organism = Homo sapiens |

SEQUENCE: 36
GGEPS 5

| SEQ ID NO: 37 | moltype = AA   length = 7 |
|---|---|
| FEATURE | Location/Qualifiers |
| source | 1..7<br>mol_type = protein<br>organism = Homo sapiens |

SEQUENCE: 37
GGEGGGP 7

| SEQ ID NO: 38 | moltype = AA   length = 12 |
|---|---|
| FEATURE | Location/Qualifiers |
| source | 1..12<br>mol_type = protein<br>organism = Homo sapiens |

SEQUENCE: 38
GGEGGGSEGG GS 12

-continued

| | | |
|---|---|---|
| SEQ ID NO: 39<br>FEATURE<br>source | moltype = AA length = 7<br>Location/Qualifiers<br>1..7<br>mol_type = protein<br>organism = Homo sapiens | |
| SEQUENCE: 39<br>TISGTDY | | 7 |
| SEQ ID NO: 40<br>FEATURE<br>source | moltype = AA length = 5<br>Location/Qualifiers<br>1..5<br>mol_type = protein<br>organism = Homo sapiens | |
| SEQUENCE: 40<br>GLTSN | | 5 |
| SEQ ID NO: 41<br>FEATURE<br>source | moltype = AA length = 17<br>Location/Qualifiers<br>1..17<br>mol_type = protein<br>organism = Homo sapiens | |
| SEQUENCE: 41<br>CILILGHSGA GSYQLTF | | 17 |
| SEQ ID NO: 42<br>FEATURE<br>source | moltype = AA length = 5<br>Location/Qualifiers<br>1..5<br>mol_type = protein<br>organism = Homo sapiens | |
| SEQUENCE: 42<br>LNHDA | | 5 |
| SEQ ID NO: 43<br>FEATURE<br>source | moltype = AA length = 7<br>Location/Qualifiers<br>1..7<br>mol_type = protein<br>organism = Homo sapiens | |
| SEQUENCE: 43<br>SQIVNDF | | 7 |
| SEQ ID NO: 44<br>FEATURE<br>source | moltype = AA length = 15<br>Location/Qualifiers<br>1..15<br>mol_type = protein<br>organism = Homo sapiens | |
| SEQUENCE: 44<br>CASSPWTSGS REQYF | | 15 |
| SEQ ID NO: 45<br>FEATURE<br>source | moltype = AA length = 17<br>Location/Qualifiers<br>1..17<br>mol_type = protein<br>organism = Homo sapiens | |
| SEQUENCE: 45<br>CILILGHSRA GNYIATF | | 17 |
| SEQ ID NO: 46<br>FEATURE<br>source | moltype = AA length = 17<br>Location/Qualifiers<br>1..17<br>mol_type = protein<br>organism = Homo sapiens | |
| SEQUENCE: 46<br>CILILGHSRL GNYIATF | | 17 |
| SEQ ID NO: 47<br>FEATURE<br>source | moltype = AA length = 17<br>Location/Qualifiers<br>1..17<br>mol_type = protein<br>organism = Homo sapiens | |
| SEQUENCE: 47<br>CILILGHSRL GNYQATF | | 17 |
| SEQ ID NO: 48<br>FEATURE<br>source | moltype = AA length = 7<br>Location/Qualifiers<br>1..7<br>mol_type = protein<br>organism = Homo sapiens | |
| SEQUENCE: 48<br>SQIMGDE | | 7 |

```
SEQ ID NO: 49              moltype = AA   length = 7
FEATURE                    Location/Qualifiers
source                     1..7
                           mol_type = protein
                           organism = Homo sapiens SEQUENCE: 49
SQIMNDE                                                                    7

SEQ ID NO: 50              moltype = AA   length = 7
FEATURE                    Location/Qualifiers
source                     1..7
                           mol_type = protein
                           organism = Homo sapiens SEQUENCE: 50
SQIVGDE                                                                    7

SEQ ID NO: 51              moltype = AA   length = 15
FEATURE                    Location/Qualifiers
source                     1..15
                           mol_type = protein
                           organism = Homo sapiens SEQUENCE: 51
CASSWWTGGA SPISF                                                          15

SEQ ID NO: 52              moltype = AA   length = 15
FEATURE                    Location/Qualifiers
source                     1..15
                           mol_type = protein
                           organism = Homo sapiens SEQUENCE: 52
CASSWWTSGA SPISF                                                          15

SEQ ID NO: 53              moltype = AA   length = 15
FEATURE                    Location/Qualifiers
source                     1..15
                           mol_type = protein
                           organism = Homo sapiens SEQUENCE: 53
CASSWWTGGS APIRF                                                          15

SEQ ID NO: 54              moltype = AA   length = 15
FEATURE                    Location/Qualifiers
source                     1..15
                           mol_type = protein
                           organism = Homo sapiens SEQUENCE: 54
CASSWWTSGS APIRF                                                          15

SEQ ID NO: 55              moltype = AA   length = 15
FEATURE                    Location/Qualifiers
source                     1..15
                           mol_type = protein
                           organism = Homo sapiens SEQUENCE: 55
CASSWWTGGS AEIRF                                                          15

SEQ ID NO: 56              moltype = AA   length = 15
FEATURE                    Location/Qualifiers
source                     1..15
                           mol_type = protein
                           organism = Homo sapiens SEQUENCE: 56
CASSWWTGGS APIYF                                                          15

SEQ ID NO: 57              moltype = AA   length = 15
FEATURE                    Location/Qualifiers
source                     1..15
                           mol_type = protein
                           organism = Homo sapiens SEQUENCE: 57
CASSWWTGGA APISF                                                          15

SEQ ID NO: 58              moltype = AA   length = 15
FEATURE                    Location/Qualifiers
source                     1..15
                           mol_type = protein
                           organism = Homo sapiens

SEQUENCE: 58
```

-continued

```
CASSWWTGGA SPIRF                                                       15

SEQ ID NO: 59          moltype = AA  length = 15
FEATURE                Location/Qualifiers
source                 1..15
                       mol_type = protein
                       organism = Homo sapiens
SEQUENCE: 59
CASSWWTGGA APIRF                                                       15

SEQ ID NO: 60          moltype = AA  length = 15
FEATURE                Location/Qualifiers
source                 1..15
                       mol_type = protein
                       organism = Homo sapiens
SEQUENCE: 60
CASSWWTGGA SEISF                                                       15

SEQ ID NO: 61          moltype = AA  length = 15
FEATURE                Location/Qualifiers
source                 1..15
                       mol_type = protein
                       organism = Homo sapiens
SEQUENCE: 61
CASSWWTGGS APISF                                                       15

SEQ ID NO: 62          moltype = AA  length = 15
FEATURE                Location/Qualifiers
source                 1..15
                       mol_type = protein
                       organism = Homo sapiens
SEQUENCE: 62
CASSWWTGGS SPISF                                                       15

SEQ ID NO: 63          moltype = AA  length = 15
FEATURE                Location/Qualifiers
source                 1..15
                       mol_type = protein
                       organism = Homo sapiens
SEQUENCE: 63
CASSPWTGGS APIRF                                                       15

SEQ ID NO: 64          moltype = AA  length = 15
FEATURE                Location/Qualifiers
source                 1..15
                       mol_type = protein
                       organism = Homo sapiens
SEQUENCE: 64
CASSWWTGGS SPIRF                                                       15
```

T CELL RECEPTORS

CROSS-REFERENCE TO RELATED APPLICATIONS

This application is a continuation of U.S. application Ser. No. 16/624,853 filed Dec. 19, 2019, which is the National Stage of International Application No. PCT/EP2018/066287, filed Jun. 19, 2018, which claims the benefit of and priority to Great Britain Patent Application Ser. No. 1709866.6, filed on Jun. 20, 2017, the contents of which are incorporated by reference in their entirety.

SEQUENCE LISTING

The instant application contains a Sequence Listing which has been submitted via Patent Center and is hereby incorporated by reference in its entirety. Said XML copy, created on Sep. 6, 2023, is named 54811 US_XML_sequence-listing.xml, and is 61,009 bytes in size.

The present invention relates to T cell receptors (TCRs) that bind the HLA-A*02 restricted peptide SLLQHLIGL (SEQ ID NO: 1) derived from the germline cancer antigen PRAME. Said TCRs may comprise non-natural mutations within the alpha and/or beta variable domains relative to a native PRAME TCR. The TCRs of the invention are particularly suitable for use as novel immunotherapeutic reagents for the treatment of malignant disease.

BACKGROUND TO THE INVENTION

T cell receptors (TCRs) are naturally expressed by $CD4^+$ and $CD8^+$ T cells. TCRs are designed to recognize short peptide antigens that are displayed on the surface of antigen presenting cells in complex with Major Histocompatibility Complex (MHC) molecules (in humans, MHC molecules are also known as Human Leukocyte Antigens, or HLA) (Davis et al., Annu Rev Immunol. 1998; 16:523-44). $CD8^+$ T cells, which are also termed cytotoxic T cells, have TCRs that specifically recognize peptides bound to MHC class I molecules. $CD8^+$ T cells are generally responsible for finding and mediating the destruction of diseased cells, including cancerous and virally infected cells. The affinity of cancer-specific TCRs in the natural repertoire for corresponding antigen is typically low as a result of thymic selection, meaning that cancerous cells frequently escape detection and destruction. Novel immunotherapeutic approaches aimed at promoting cancer recognition by T cells offer a highly promising strategy for the development of effective anticancer treatments.

PRAME or Preferentially Expressed Antigen In Melanoma was first identified as an antigen that is over expressed in melanoma (Ikeda et al Immunity. 1997 February; 6(2): 199-208); it is also known as CT130, MAPE, OIP-4 and has Uniprot accession number P78395. The protein functions as a repressor of retinoic acid receptor signalling (Epping et al., Cell. 2005 Sep. 23; 122(6):835-47). PRAME belongs to the family of germline-encoded antigens known as cancer testis antigens. Cancer testis antigens are attractive targets for immunotherapeutic intervention since they typically have limited or no expression in normal adult tissues. PRAME is expressed in a number of solid tumours as well as in leukaemias and lymphomas (Doolan et al Breast Cancer Res Treat. 2008 May; 109(2):359-65; Epping et al Cancer Res. 2006 Nov. 15; 66(22):10639-42; Ercolak et al Breast Cancer Res Treat. 2008 May; 109(2):359-65; Matsushita et al Leuk Lymphoma. 2003 March; 44(3):439-44; Mitsuhashi et al Int. J Hematol. 2014; 100(1):88-95; Proto-Sequeire et al Leuk Res. 2006 November; 30(11):1333-9; Szczepanski et al Oral Oncol. 2013 February; 49(2):144-51; Van Baren et al Br J Haematol. 1998 September; 102(5):1376-9). PRAME targeting therapies of the inventions may be particularly suitable for treatment cancers including, but not limited to, lung (NSCLC and SCLC), breast (including triple negative), ovarian, endometrial, oesophageal, bladder and head and neck cancers.

The peptide SLLQHLIGL (SEQ ID NO: 1) corresponds to amino acids 425-433 of the full length PRAME protein and is presented on the cell surface in complex with HLA-A*02 (Kessler et al., J Exp Med. 2001 Jan. 1; 193(1):73-88). This peptide-HLA complex provides a useful target for TCR-based immunotherapeutic intervention.

The identification of particular TCR sequences that bind to the SLLQHLIGL (SEQ ID NO: 1) HLA-A*02 complex with high affinity and high specificity is advantageous for the development of novel immunotherapies. Therapeutic TCRs may be used, for example, as soluble targeting agents for the purpose of delivering cytotoxic agents to the tumour site or activating immune effector functions against the tumour cells (Lissin, et al., "High-Affinity Monoclonal T-cell receptor (mTCR) Fusions" in Fusion Protein Technologies for Biophamaceuticals: Applications and Challenges. 2013. S. R. Schmidt, Wiley; Boulter et al., Protein Eng. 2003 September; 16(9):707-11; Liddy, et al., Nat Med. 2012 June; 18(6):980-7), or alternatively they may be used to engineer T cells for adoptive therapy (Fesnak et al., Nat Rev Cancer. 2016 Aug. 23; 16(9):566-81).

TCRs that bind to SLLQHLIGL (SEQ ID NO: 1) in complex with HLA-A*02 have been reported previously (Amir et al., Clin Cancer Res. 2011 Sep. 1; 17(17):5615-25; Griffioen et al., Clin Cancer Res. 2006 May 15; 12(10): 3130-6; WO2016142783). However, these TCRs have not been engineered so that they bind to the target antigen with increased affinity, relative to the natural TCR. As explained further below, supra-physiological antigen affinity is a desirable feature for a therapeutic TCR, the production of which is not straightforward, particularly when balanced with other desirable features, such as specificity.

The TCR sequences defined herein are described with reference to IMGT nomenclature which is widely known and accessible to those working in the TCR field. For example, see: LeFranc and LeFranc, (2001). "T cell Receptor Factsbook", Academic Press; Lefranc, (2011), Cold Spring Harb Protoc 2011(6): 595-603; Lefranc, (2001), Curr Protoc Immunol Appendix 1: Appendix 100; and Lefranc, (2003), Leukemia 17(1): 260-266. Briefly, (α TCRs consist of two disulphide linked chains. Each chain (alpha and beta) is generally regarded as having two domains, namely a variable and a constant domain. A short joining region connects the variable and constant domains and is typically considered part of the alpha variable region. Additionally, the beta chain usually contains a short diversity region next to the joining region, which is also typically considered part of the beta variable region.

The variable domain of each chain is located N-terminally and comprises three Complementarity Determining Regions (CDRs) embedded in a framework sequence (FR). The CDRs comprise the recognition site for peptide-MHC binding. There are several genes coding for alpha chain variable (Vα) regions and several genes coding for beta chain variable (Vβ) regions, which are distinguished by their framework, CDR1 and CDR2 sequences, and by a partly defined CDR3 sequence. The Vα and Vβ genes are referred to in IMGT nomenclature by the prefix TRAV and TRBV respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000), Exp Clin Immunogenet 17(2): 107-114; Scaviner and Lefranc, (2000), Exp Clin Immunogenet 17(2): 97-106; LeFranc and LeFranc, (2001), "T cell Receptor Factsbook", Academic Press). The huge diversity of T cell receptor chains results from combinatorial rearrangements between the various V, J and D genes, which include allelic variants, and junctional diversity (Arstila, et al., (1999), Science 286(5441): 958-961; Robins et al., (2009), Blood 114(19): 4099-4107.) The constant, or C, regions of TCR alpha and beta chains are referred to as TRAC and TRBC respectively (Lefranc, (2001), Curr Protoc Immunol Appendix 1: Appendix 10).

The inventors of the present application have surprisingly found novel TCRs that are able to bind to SLLQHLIGL (SEQ ID NO: 1)-HLA-A*02 complex with high affinity and specificity. Said TCRs are engineered from a suitable scaffold sequence into which a number of mutations are introduced. The TCRs of the invention have a particularly suitable profile for therapeutic use. In general, the identification of such TCRs is not straightforward and typically has a high attrition rate.

In the first instance, the skilled person needs to identify a suitable starting, or scaffold, sequence. Typically such sequences are obtained from natural sources e.g. from antigen responding T cells extracted from donor blood. Given the rarity of cancer specific T cells in the natural repertoire, it is often necessary to screen many donors, for example 20 or more, before a responding T cell may be found. The screening process may take several weeks or months, and even where a responding T cell is found, it may be unsuitable for immunotherapeutic use. For example, the response may be too weak and/or may not be specific for the target antigen. Alternatively, it may not be possible to generate a clonal T cell population, nor expand or maintain a given T cell line to produce sufficient material to identify the correct TCR chain sequences. TCR sequences that are suitable as starting, or scaffold, sequences should have one or more of the following properties: a good affinity for the target peptide-HLA complex, for example 200 μM or stronger; a high level of target specificity, e.g. relatively weak or no binding to alternative peptide-HLA complexes; be amenable to use in display libraries, such as phage display; and be able to be refolded and purified at high yield. Given the degenerate nature of TCR recognition, it is exceptionally hard even for skilled practitioners to be able to determine whether a particular scaffold TCR sequence has a specificity profile that would make it eligible for engineering for therapeutic use (Wooldridge, et al., J Biol Chem. 2012 Jan. 6; 287(2):1168-77).

The next challenge is to engineer the TCR to have a higher affinity towards the target antigen whilst retaining desirable characteristics such as specificity and yield. TCRs, as they exist in nature, have weak affinity for target antigen (low micromolar range) compared with antibodies, and TCRs against cancer antigens typically have weaker antigen recognition than viral specific TCRs (Aleksic, et al. Eur J Immunol. 2012 December; 42(12):3174-9). This weak affinity coupled with HLA down-regulation on cancer cells means that therapeutic TCRs for cancer immunotherapy typically require engineering to increase their affinity for target antigen and thus generate a more potent response. Such affinity increases are essential for soluble TCR-based reagents. In such cases, antigen-binding affinities in the nanomolar to picomolar range, with binding half-lives of several hours, are desirable. The improved potency generated by high affinity antigen recognition at low epitope numbers is exemplified in FIGS. 1e and 1f of Liddy et al. (Liddy, et al., Nat Med. 2012 June; 18(6):980-7). The affinity maturation process, typically involves the skilled person having to engineer specific mutations and/or combinations of mutations, including but not limited to substitutions, insertions and/or deletions, on to the starting TCR sequence in order to increase the strength of antigen recognition. Methods to engineer affinity enhancing mutations on to a given TCR are known in the art, for example the use of display libraries (Li et al., Nat Biotechnol. 2005 March; 23(3):349-54; Holler et al., Proc Natl Acad Sci USA. 2000 May 9; 97(10):5387-92). However, to produce significant increases in the affinity of a given TCR against a given target, the skilled person may have to engineer combinations of mutations from a large pool of possible alternatives. The specific mutations and/or combinations of mutations that produce significant increases in affinity are not predictable and there is a high attrition rate. In many cases, it may not be possible to achieve significant increases in affinity with a given TCR starting sequence.

The affinity maturation process must also take account of the necessity of maintaining TCR antigen specificity. Increasing the affinity of a TCR for its target antigen brings a substantial risk of revealing cross reactivity with other unintended targets as a result of the inherent degeneracy of TCR antigen recognition (Wooldridge, et al., J Biol Chem. 2012 Jan. 6; 287(2):1168-77; Wilson, et al., Mol Immunol. 2004 February; 40(14-15):1047-55; Zhao et al., J Immunol. 2007 Nov. 1; 179(9):5845-54). At a natural level of affinity the recognition of the cross reactive antigen may be too low to produce a response. If a cross reactive antigen is displayed on normal healthy cells, there is a strong possibility of off-target binding in vivo which may manifest in clinical toxicity. Thus, in addition to increasing antigen binding strength, the skilled person must also engineer mutations and or combinations of mutations that allow the TCR to retain a high specificity for target antigen and demonstrate a good safety profile in preclinical testing. Again, suitable mutations and/or combinations of mutations are not predictable. The attrition rate at this stage is even higher and in many cases may not be achievable at all from a given TCR starting sequence.

Despite the difficulties described above, the inventors have identified mutated TCRs with a particularly high affinity (picomolar range), and a high degree of antigen specificity. Said TCRs demonstrate potent killing of PRAME positive cancer cells when prepared as soluble reagents fused to a T cell redirecting moiety.

DESCRIPTION OF THE INVENTION

In a first aspect, the present invention provides a T cell receptor (TCR) having the property of binding to SLLQH- LIGL (SEQ ID NO: 1) in complex with HLA-A*02 and comprising a TCR alpha chain variable domain and/or a TCR beta chain variable domain, each of which comprises FR1-CDR1-FR2-CDR2-FR3-CDR3-FR4 where FR is a framework region and CDR is a complementarity determining region, wherein (a) the alpha chain CDRs have the following sequences:

```
                                    (SEQ ID NO: 39)
CDR1 - TISGTDY (SEQ ID NO: 40)
CDR2 - GLTSN (SEQ ID NO: 41)
CDR3 - CILILGHSGAGSYQLTF
``` optionally with one or more mutations therein, and/or
(b) the beta chain CDRs have the following sequences:

```
                                    (SEQ ID NO: 42)
CDR1 - LNHDA (SEQ ID NO: 43)
CDR2 - SQIVNDF (SEQ ID NO: 44)
CDR3 - CASSPWTSGSREQYF
``` optionally with one or more mutations therein.

In the TCR of the first aspect, the alpha chain variable domain framework regions may comprise the following framework sequences:

FR1—amino acids 1-25 of SEQ ID NO: 2
FR2—amino acids 33-49 of SEQ ID NO: 2
FR3—amino acids 55-87 of SEQ ID NO: 2
FR4—amino acids 105-114 of SEQ ID NO: 2 or respective sequences having at least 90, 91, 92, 93, 94, 95, 96, 97, 98 or 99% identity to said sequences, and/or the beta chain variable domain framework regions may comprise the following sequences:

FR1—amino acids 1-26 of SEQ ID NO: 3
FR2—amino acids 32-48 of SEQ ID NO: 3
FR3—amino acids 56-90 of SEQ ID NO: 3
FR4—amino acids 106-114 of SEQ ID NO: 3 or respective sequences having at least 90, 91, 92, 93, 94, 95, 96, 97, 98 or 99% identity to said sequences.

The term 'mutations' encompasses substitutions, insertions and deletions. Mutations to a parental (or wild type, or scaffold) TCR may include those that increase the binding affinity ($k_D$ and/or binding half life) of the TCR to SLLQH-LIGL (SEQ ID NO: 1)-HLA-A*02 complex.

Conventionally, beta chain residue F55 is considered to be part of framework region 3. However, for the purposes of the present invention, beta chain residue F55 is considered part of CDR2.

The alpha chain framework regions FR1, FR2, and FR3 may comprise amino acid sequences corresponding to a TRAV 26-2 chain and/or the beta chain framework regions FR1, FR2 and FR3, may comprise amino acid sequences corresponding to those of a TRBV19 chain.

The FR4 region may comprise the joining region of the alpha and beta variable chains (TRAJ and TRBJ, respectively).

In the TCR alpha chain variable region, there may be at least one mutation. There may be one, two, three, four or five, or more, mutations in the alpha chain CDRs. There may be one, two, three, four or five mutations in the alpha chain CDR3. One or more of said mutations may be selected from the following mutations, with reference to the numbering of SEQ ID NO: 2:

| Wild type | Mutation |
| --- | --- |
| G96 (CDR3) | R |
| A97 (CDR3) | L |
| S99 (CDR3) | N |
| Q101 (CDR3) | I |
| L102 (CDR3) | A |

Thus, there may be any or all of the mutations in the table above, optionally in combination with other mutations.

The alpha chain CDR3 may comprise one of the following groups of mutations (with reference to the numbering of SEQ ID NO: 2):

| | | | | | |
| --- | --- | --- | --- | --- | --- |
| 1 | G96R |      | S99N | Q101I | L102A |
| 2 | G96R | A97L | S99N | Q101I | L102A |
| 3 | G96R | A97L | S99N |       | L102A |

A preferred group of mutations is group 1. Another preferred group of mutations is group 2.

The alpha chain CDR3 may have a sequence selected from:

```
                                    (SEQ ID NO: 45)
CILILGHSRAGNYIATF (SEQ ID NO: 46)
CILILGHSRLGNYIATF (SEQ ID NO: 47)
CILILGHSRLGNYQATF
```

A preferred alpha chain CDR3 is CILILGHSRAGNYIATF (SEQ ID NO: 45). A preferred alpha chain CDR3 is CILILGHSRLGNYIATF (SEQ ID NO: 46).

In the TCR beta chain variable region, there may be at least one mutation. There may be one, two, three, four, five, six, seven, eight, nine 10, or more, mutations in the beta chain CDRs. There may be one, two, three, four, five, six, seven, eight, nine or ten mutations in the beta chain CDR3. One or more of said mutations may be selected from the following mutations with reference to the numbering of SEQ ID NO: 3:

| Wild type | Mutation |
| --- | --- |
| V52 (CDR2) | M |
| N53 (CDR2) | G |
| F55 (CDR2) | E |
| P95 (CDR3) | W |
| S98 (CDR3) | G |
| S100 (CDR3) | A |
| R101 (CDR3) | S or A |
| E102 (CDR3) | P |
| Q103 (CDR3) | I |
| Y104 (CDR3) | S or R |

Thus, there may be any or all of the mutations in the table above, optionally in combination with other mutations.

The beta chain CDR2 and CDR3 may comprise one of the following groups of mutations (with reference to the numbering of SEQ ID NO: 3):

| | | | | | | | | | |
|---|---|---|---|---|---|---|---|---|---|
| 1 | V52M | N53G | F55E | P95W | S98G | S100A | R101S | E102P | Q103I | Y104S |
| 2 | V52M | N53G | F55E | P95W | | S100A | R101S | E102P | Q103I | Y104S |
| 3 | V52M | N53G | F55E | P95W | S98G | | R101A | E102P | Q103I | Y104R |
| 4 | V52M | | F55E | P95W | S98G | | R101A | E102P | Q103I | Y104R |
| 5 | V52M | N53G | F55E | P95W | | | R101A | E102P | Q103I | Y104R |
| 6 | V52M | N53G | F55E | P95W | S98G | | R101A | | Q103I | Y104R |
| 7 | V52M | N53G | F55E | P95W | S98G | | R101A | E102P | Q103I | |
| 8 | V52M | N53G | F55E | P95W | S98G | S100A | R101A | E102P | Q103I | Y104S |
| 9 | V52M | N53G | F55E | P95W | S98G | S100A | R101S | E102P | Q103I | Y104R |
| 10 | V52M | N53G | F55E | P95W | S98G | S100A | R101A | E102P | Q103I | Y104R |
| 11 | V52M | N53G | F55E | P95W | S98G | S100A | R101S | | Q103I | Y104S |
| 12 | V52M | N53G | F55E | P95W | S98G | | R101A | E102P | Q103I | Y104S |
| 13 | V52M | N53G | F55E | P95W | S98G | | R101S | E102P | Q103I | Y104S |
| 14 | | N53G | F55E | P95W | S98G | | R101A | E102P | Q103I | Y104R |
| 15 | V52M | N53G | F55E | | S98G | | R101A | E102P | Q103I | Y104R |
| 16 | V52M | N53G | F55E | P95W | S98G | | R101S | E102P | Q103I | Y104R |

A preferred group of mutations is group 1. A preferred group of mutations is group 9.

The beta chain CDR2 may have a sequence selected from:

SQIMGDE (SEQ ID NO: 48)

SQIMNDE (SEQ ID NO: 49)

SQIVGDE (SEQ ID NO: 50)

A preferred beta chain CDR2 is SQIMGDE (SEQ ID NO: 48).

The beta chain CDR3 may have a sequence selected from:

CASSWWTGGASPISF (SEQ ID NO: 51)

CASSWWTSGASPISF (SEQ ID NO: 52)

CASSWWTGGASPIRF (SEQ ID NO: 53)

CASSWWTSGSAPIRF (SEQ ID NO: 54)

CASSWWTGGSAEIRF (SEQ ID NO: 55)

CASSWWTGGSAPIYF (SEQ ID NO: 56)

CASSWWTGGAAPISF (SEQ ID NO: 57)

CASSWWTGGASPIRF (SEQ ID NO: 58)

CASSWWTGGAAPIRF (SEQ ID NO: 59)

CASSWWTGGASEISF (SEQ ID NO: 60)

CASSWWTGGSAPISF (SEQ ID NO: 61)

CASSWWTGGSSPISF (SEQ ID NO: 62)

CASSPWTGGSAPIRF (SEQ ID NO: 63)

CASSWWTGGSSPIRF (SEQ ID NO: 64)

A preferred beta chain CDR3 is CASSWWTGGASPISF (SEQ ID NO: 51). A preferred beta chain CDR3 is CASSWWTGGASPIRF (SEQ ID NO: 58).

Preferred combinations of beta chain CDR2 and CDR3 are as follows:

| | | |
|---|---|---|
| 1 | SQIMGDE (SEQ ID NO: 48) | CASSWWTGGASPISF (SEQ ID NO: 51) |
| 2 | SQIMGDE (SEQ ID NO: 48) | CASSWWTSGASPISF (SEQ ID NO: 52) |
| 3 | SQIMGDE (SEQ ID NO: 48) | CASSWWTGGASPIRF (SEQ ID NO: 53) |
| 4 | SQIMNDE (SEQ ID NO: 49) | CASSWWTGGASPIRF (SEQ ID NO: 53) |
| 5 | SQIMGDE (SEQ ID NO: 48) | CASSWWTSGSAPIRF (SEQ ID NO: 54) |
| 6 | SQIMGDE (SEQ ID NO: 48) | CASSWWTGGSAEIRF (SEQ ID NO: 55) |
| 7 | SQIMGDE (SEQ ID NO: 48) | CASSWWTGGSAPIYF (SEQ ID NO: 56) |
| 8 | SQIMGDE (SEQ ID NO: 48) | CASSWWTGGAAPISF (SEQ ID NO: 57) |
| 9 | SQIMGDE (SEQ ID NO: 48) | CASSWWTGGASPIRF (SEQ ID NO: 58) |
| 10 | SQIMGDE (SEQ ID NO: 48) | CASSWWTGGAAPIRF (SEQ ID NO: 59) |
| 11 | SQIMGDE (SEQ ID NO: 48) | CASSWWTGGASEISF (SEQ ID NO: 60) |
| 12 | SQIMGDE (SEQ ID NO: 48) | CASSWWTGGSAPISF (SEQ ID NO: 61) |

-continued

| | | |
|---|---|---|
| 13 | SQIMGDE (SEQ ID NO: 48) | CASSWWTGGSSPISF (SEQ ID NO: 62) |
| 14 | SQIVGDE (SEQ ID NO: 50) | CASSWWTGGSAPIRF (SEQ ID NO: 53) |
| 15 | SQIMGDE (SEQ ID NO: 48) | CASSPWTGGSAPIRF (SEQ ID NO: 63) |
| 16 | SQIMGDE (SEQ ID NO: 48) | CASSWWTGGSSPIRF (SEQ ID NO: 64) |

A preferred combination is combination 1. Another preferred combination is combination 9.

In a preferred embodiment, the TCR alpha and beta chain CDR sequences are selected from:

| | Alpha | | | Beta | | |
|---|---|---|---|---|---|---|
| | CDR1 | CDR2 | CDR3 | CDR1 | CDR2 | CDR3 |
| 1 | TISGTDY (SEQ ID NO: 39) | GLTSN (SEQ ID NO: 40) | CILILGHSRAGNYIATF (SEQ ID NO: 45) | LNHDA (SEQ ID NO: 42) | SQIMGDE (SEQ ID NO: 48) | CASSWWTGGASPISF (SEQ ID NO: 51) |
| 2 | TISGTDY (SEQ ID NO: 39) | GLTSN (SEQ ID NO: 40) | CILILGHSRAGNYIATF (SEQ ID NO: 45) | LNHDA (SEQ ID NO: 42) | SQIMGDE (SEQ ID NO: 48) | CASSWWTGGASEISF (SEQ ID NO: 60) |
| 3 | TISGTDY (SEQ ID NO: 39) | GLTSN (SEQ ID NO: 40) | CILILGHSRAGNYIATF (SEQ ID NO: 45) | LNHDA (SEQ ID NO: 42) | SQIMGDE (SEQ ID NO: 48) | CASSWWTGGASPIRF (SEQ ID NO: 58) |
| 4 | TISGTDY (SEQ ID NO: 39) | GLTSN (SEQ ID NO: 40) | CILILGHSRAGNYIATF (SEQ ID NO: 45) | LNHDA (SEQ ID NO: 42) | SQIMGDE (SEQ ID NO: 48) | CASSWWTGGSAPISF (SEQ ID NO: 61) |
| 5 | TISGTDY (SEQ ID NO: 39) | GLTSN (SEQ ID NO: 40) | CILILGHSRAGNYIATF (SEQ ID NO: 45) | LNHDA (SEQ ID NO: 42) | SQIMGDE (SEQ ID NO: 48) | CASSWWTSGASPISF (SEQ ID NO: 52) |
| 6 | TISGTDY (SEQ ID NO: 39) | GLTSN (SEQ ID NO: 40) | CILILGHSRAGNYIATF (SEQ ID NO: 45) | LNHDA (SEQ ID NO: 42) | SQIMGDE (SEQ ID NO: 48) | CASSWWTGGSSPISF (SEQ ID NO: 62) |
| 7 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGSAPIRF (SEQ ID NO: 53) |
| 8 | TISGTDY (SEQ ID NO: 39) | GLTSN (SEQ ID NO: 40) | CILILGHSRLGNYQATF (SEQ ID NO: 47) | LNHDA (SEQ ID NO: 42) | SQIMGDE (SEQ ID NO: 48) | CASSWWTGGSAPIRF (SEQ ID NO: 53) |
| 9 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIVGDE (SEQ ID NO: 50) | CASSWWTGGSAPIRF (SEQ ID NO: 53) |
| 10 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMNDE (SEQ ID NO: 49) | CASSWWTGGSAPIRF (SEQ ID NO: 53) |
| 11 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSPWTGGSAPIRF (SEQ ID NO: 63) |
| 12 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTSGSAPIRF (SEQ ID NO: 54) |
| 13 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGSAEIRF (SEQ ID NO: 55) |
| 14 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGSAPIYF (SEQ ID NO: 56) |
| 15 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGSSPISF (SEQ ID NO: 62) |

-continued

| | Alpha | | | Beta | | |
|---|---|---|---|---|---|---|
| | CDR1 | CDR2 | CDR3 | CDR1 | CDR2 | CDR3 |
| 16 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGAAPISF (SEQ ID NO: 57) |
| 17 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGASPIRF (SEQ ID NO: 58) |
| 18 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGSAPISF (SEQ ID NO: 61) |
| 19 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGSSPIRF (SEQ ID NO: 64) |
| 20 | TISGTDY (SEQ ID NO: 39) | GLTSN (SEQ ID NO: 40) | CILILGHSRLGNYIATF (SEQ ID NO: 46) | LNHDA (SEQ ID NO: 42) | SQIMGDE (SEQ ID NO: 48) | CASSWWTGGAPIRF (SEQ ID NO: 59) |

A preferred combination is combination 1. A preferred combination is combination 17.

Mutation(s) within the CDRs preferably improve the binding affinity of the TCR to the SLLQHLIGL (SEQ ID NO: 1)-HLA-A*02 complex, but may additionally or alternatively confer other advantages such as improved stability in an isolated form and improved specificity. Mutations at one or more positions may additionally or alternatively affect the interaction of an adjacent position with the cognate pMHC complex, for example by providing a more favourable angle for interaction. Mutations may include those that are able to reduce the amount of non-specific binding, i.e. reduce binding to alternative antigens relative to SLLQHLIGL (SEQ ID NO: 1)-HLA-A*02. Mutations may include those that increase efficacy of folding and/or manufacture. Some mutations may contribute to each of these characteristics; others may contribute to affinity but not to specificity, for example, or to specificity but not to affinity etc.

Typically, at least 5, at least 10, at least 15, or more CDR mutations in total are needed to obtain TCRs with pM affinity for target antigen. At least 5, at least 10 or at least 15 CDR mutations in total may be needed to obtain TCRs with pM affinity for target antigen. TCRs with pM affinity for target antigen are especially suitable as soluble therapeutics. TCRs for use in adoptive therapy applications may have lower affinity for target antigen and thus fewer CDR mutations, for example, up to 1, up to 2, up to 5, or more CDR mutations in total. TCRs for use in adoptive therapy applications may have lower affinity for target antigen and thus fewer CDR mutations, for example, up to 1, up to 2 or up to 5 CDR mutations in total.

Mutations may additionally, or alternatively, be made outside of the CDRs, within the framework regions; such mutations may improve binding, and/or specificity, and/or stability, and/or the yield of a purified soluble form of the TCR. For example, the TCR of the invention may, additionally or alternatively, comprise an alpha chain variable domain, wherein the alpha chain variable region FR1 has a G residue at position −1 using the numbering of SEQ ID NO: 2, i.e. inserted before position 1. It was found that a G at position −1 improves cleavage efficiency of the N-terminal methionine during production in E. coli. Inefficient cleavage may be detrimental for a therapeutic, since it may result in a heterogeneous protein product, and or the presence of the initiation methionine may be immunogenic in humans.

Preferably, the α chain variable domain of the TCR of the invention may comprise respective framework amino acid sequences that have at least 90%, at least 91%, at least 92%, at least 93%, at least 94%, at least 95%, at least 96%, at least 97%, at least 98% or at least 99% identity to the framework amino acid residues 1-25, 33-49, 55-87, 105-114 of SEQ ID NO: 2. The beta chain variable domain of the TCR of the invention may comprise respective framework amino acid sequences that have at least 90%, at least 91%, at least 92%, at least 93%, at least 94%, at least 95%, at least 96%, at least 97%, at least 98% or at least 99% identity to the framework amino acid residues 1-26, 32-48, 56-90, 106-114 of SEQ ID NO: 3. Alternatively, the stated percentage identity may be over the framework sequences when considered as a whole.

The alpha chain variable domain may comprise any one of the amino acid sequences of SEQ ID NOs: 6-8 and the beta chain variable domain may comprise any one of the amino acid sequences of SEQ ID NOs: 9-24.

For example, the TCR may comprise the following alpha and beta chain pairs.

| Alpha chain variable domain | Beta chain variable domain |
|---|---|
| SEQ ID NO: 6 | SEQ ID NO: 9 |
| SEQ ID NO: 6 | SEQ ID NO: 19 |
| SEQ ID NO: 6 | SEQ ID NO: 17 |
| SEQ ID NO: 6 | SEQ ID NO: 20 |
| SEQ ID NO: 6 | SEQ ID NO: 10 |
| SEQ ID NO: 6 | SEQ ID NO: 21 |
| SEQ ID NO: 7 | SEQ ID NO: 11 |
| SEQ ID NO: 8 | SEQ ID NO: 11 |
| SEQ ID NO: 7 | SEQ ID NO: 22 |
| SEQ ID NO: 7 | SEQ ID NO: 12 |
| SEQ ID NO: 7 | SEQ ID NO: 23 |
| SEQ ID NO: 7 | SEQ ID NO: 13 |
| SEQ ID NO: 7 | SEQ ID NO: 14 |
| SEQ ID NO: 7 | SEQ ID NO: 15 |
| SEQ ID NO: 7 | SEQ ID NO: 21 |
| SEQ ID NO: 7 | SEQ ID NO: 16 |

| Alpha chain variable domain | Beta chain variable domain |
|---|---|
| SEQ ID NO: 7 | SEQ ID NO: 17 |
| SEQ ID NO: 7 | SEQ ID NO: 20 |
| SEQ ID NO: 7 | SEQ ID NO: 24 |
| SEQ ID NO: 7 | SEQ ID NO: 18 |

A preferred TCR chain pairing is SEQ ID NO: 6 and SEQ ID NO: 9. A preferred TCR chain pairing is SEQ ID NO: 7 and SEQ ID NO: 17.

Within the scope of the invention are phenotypically silent variants of any TCR of the invention disclosed herein. As used herein the term "phenotypically silent variants" is understood to refer to a TCR variable domain which incorporates one or more further amino acid changes, including substitutions, insertions and deletions, in addition to those set out above, which TCR has a similar phenotype to the corresponding TCR without said change(s). For the purposes of this application, TCR phenotype comprises binding affinity ($K_D$ and/or binding half-life) and specificity. Preferably, the phenotype for a soluble TCR associated with an immune effector includes potency of immune activation and purification yield, in addition to binding affinity and specificity. A phenotypically silent variant may have a $K_D$ and/or binding half-life for the SLLQHLIGL (SEQ ID NO: 1)-HLA-A*02 complex within 50%, or more preferably within 30%, 25% or 20%, of the measured $K_D$ and/or binding half-life of the corresponding TCR without said change(s), when measured under identical conditions (for example at 25° C. and/or on the same SPR chip). Suitable conditions are further provided in Example 3. As is known to those skilled in the art, it may be possible to produce TCRs that incorporate changes in the variable domains thereof compared to those detailed above without altering the affinity of the interaction with the SLLQHLIGL (SEQ ID NO: 1)-HLA-A*02 complex, and or other functional characteristics. In particular, such silent mutations may be incorporated within parts of the sequence that are known not to be directly involved in antigen binding (e.g. the framework regions and or parts of the CDRs that do not contact the antigen). Such variants are included in the scope of this invention.

Phenotypically silent variants may contain one or more conservative substitutions and/or one or more tolerated substitutions. By tolerated substitutions it is meant those substitutions which do not fall under the definition of conservative as provided below but are nonetheless phenotypically silent. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

Substitutions of this nature are often referred to as "conservative" or "semi-conservative" amino acid substitutions. The present invention therefore extends to use of a TCR comprising any of the amino acid sequence described above but with one or more conservative substitutions and or one or more tolerated substitutions in the sequence, such that the amino acid sequence of the TCR has at least 90% identity, such as 90%, 91%, 92%, 93%, 94%, 95%, 96%, 97%, 98%, 99% or 100% identity, to the TCR comprising amino acids 1-114 of SEQ ID NOs: 2, 6-8, and/or amino acids 1-114 of SEQ ID NOs: 3,9-24.

Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad.

Sci. USA 87:2264-2268, modified as in Karlin and Altschul (1993) Proc. Natl. Acad. Sci. USA 90:5873-5877. The BLASTn and BLASTp programs of Altschul, et al. (1990) J. Mol. Biol. 215:403-410 have incorporated such an algorithm. Determination of percent identity between two nucleotide sequences can be performed with the BLASTn program. Determination of percent identity between two protein sequences can be performed with the BLASTp program. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., BLASTp and BLASTp) can be used. See http #www.ncbi.nlm.nih.gov. Default general parameters may include for example, Word Size=3, Expect Threshold=10. Parameters may be selected to automatically adjust for short input sequences. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search. For the purposes of evaluating percent identity in the present disclosure, BLASTp with the default parameters is used as the comparison methodology. In addition, when the recited percent identity provides a non-whole number value for amino acids (i.e., a sequence of 25 amino acids having 90% sequence identity provides a value of "22.5", the obtained value is rounded down to the next whole number, thus "22"). Accordingly, in the example provided, a sequence having 22 matches out of 25 amino acids is within 90% sequence identity.

As will be obvious to those skilled in the art, it may be possible to truncate, or extend, the sequences provided at the C-terminus and/or N-terminus thereof, by 1, 2, 3, 4, 5 or more residues, without substantially affecting the functional characteristics of the TCR. The sequences provided at the C-terminus and/or N-terminus thereof may be truncated or extended by 1, 2, 3, 4 or 5 residues. All such variants are encompassed by the present invention.

Mutations, including conservative and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning-A Laboratory Manual ($3^{rd}$ Ed.) CSHL Press. Further information on ligation independent cloning (LIC) procedures can be found in Rashtchian, (1995) Curr Opin Biotechnol 6(1): 30-6. The TCR sequences provided by the invention may be obtained from solid state synthesis, or any other appropriate method known in the art.

The TCRs of the invention have the property of binding the SLLQHLIGL(SEQ ID NO: 1)-HLA-A*02 complex. TCRs of the invention demonstrate a high degree of specificity for SLLQHLIGL (SEQ ID NO: 1)-HLA-A*02 complex and are thus particularly suitable for therapeutic use. Specificity in the context of TCRs of the invention relates to their ability to recognise HLA-A*02 target cells that are antigen positive, whilst having minimal ability to recognise HLA-A*02 target cells that are antigen negative.

Specificity can be measured in vitro, for example, in cellular assays such as those described in Examples 6, 7 and 8. To test specificity, the TCRs may be in soluble form and associated with an immune effector, and/or may be expressed on the surface of cells, such as T cells. Specificity may be determined by measuring the level of T cell activation in the presence of antigen positive and antigen negative target cells. Minimal recognition of antigen negative target cells is defined as a level of T cell activation of less than 20%, preferably less than 10%, preferably less than 5%, and more preferably less than 1%, of the level produced in the presence of antigen positive target cells, when measured under the same conditions and at a therapeutically relevant TCR concentration. For soluble TCRs associated with an immune effector, a therapeutically relevant concentration may be defined as a TCR concentration of $10^{-9}$ M or below, and/or a concentration of up to 100, preferably up to 1000, fold greater than the corresponding EC50 value. Preferably, for soluble TCRs associated with an immune effector there is at least a 100 fold difference in concentration required for T cell activation against antigen positive cells relative to antigen negative cells. Antigen positive cells may be obtained by peptide-pulsing using a suitable peptide concentration to obtain a level of antigen presentation comparable to cancer cells (for example, $10^{-9}$ M peptide, as described in Bossi et al., (2013) Oncoimmunol. 1; 2 (11): e26840) or, they may naturally present said peptide. Preferably, both antigen positive and antigen negative cells are human cells. Preferably antigen positive cells are human cancer cells. Antigen negative cells preferably include those derived from healthy human tissues.

Specificity may additionally, or alternatively, relate to the ability of a TCR to bind to SLLQHLIGL (SEQ ID NO: 1) HLA-A*02 complex and not to a panel of alternative peptide-HLA complexes. This may, for example, be determined by the Biacore method of Example 3. Said panel may contain at least 5, and preferably at least 10, alternative peptide-HLA-A*02 complexes. The alternative peptides may share a low level of sequence identity with SEQ ID NO: 1 and may be naturally presented. Alternative peptides are preferably derived from proteins expressed in healthy human tissues. Binding of the TCR to the SLLQHLIGL (SEQ ID NO: 1)-HLA-A*02 complex may be at least 2 fold greater than to other naturally-presented peptide HLA complexes, more preferably at least 10 fold, or at least 50 fold or at least 100 fold greater, even more preferably at least 400 fold greater.

An alternative or additional approach to determine TCR specificity may be to identify the peptide recognition motif of the TCR using sequential mutagenesis, e.g. alanine scanning. Residues that form part of the binding motif are those that are not permissible to substitution. Non-permissible substitutions may be defined as those peptide positions in which the binding affinity of the TCR is reduced by at least 50%, or preferably at least 80% relative to the binding affinity for the non-mutated peptide. Such an approach is further described in Cameron et al., (2013), Sci Transl Med. 2013 Aug. 7; 5 (197): 197ra103 and WO2014096803. TCR specificity in this case may be determined by identifying alternative motif containing peptides, particularly alternative motif containing peptides in the human proteome, and testing these peptides for binding to the TCR. Binding of the TCR to one or more alternative peptides may indicate a lack of specificity. In this case further testing of TCR specificity via cellular assays may be required.

TCRs of the invention may have an ideal safety profile for use as therapeutic reagents. In this case the TCRs may be in soluble form and may preferably be fused to an immune effector. Suitable immune effectors include but are not limited to, cytokines, such as IL-2 and IFN-γ; superantigens and mutants thereof; chemokines such as IL-8, platelet factor 4, melanoma growth stimulatory protein; antibodies, including fragments, derivatives and variants thereof, that bind to antigens on immune cells such as T cells or NK cell (e.g. anti-CD3, anti-CD28 or anti-CD16); and complement activators. An ideal safety profile means that in addition to demonstrating good specificity, the TCRs of the invention may have passed further preclinical safety tests. Examples of such tests include whole blood assays to confirm minimal cytokine release in the presence of whole blood and thus low risk of causing a potential cytokine release syndrome in vivo, and alloreactivity tests to confirm low potential for recognition of alternative HLA types.

TCRs of the invention may be amenable to high yield purification, particularly TCRs in soluble format. Yield may be determined based on the amount of material retained during the purification process (i.e. the amount of correctly folded material obtained at the end of the purification process relative to the amount of solubilised material obtained prior to refolding), and or yield may be based on the amount of correctly folded material obtained at the end of the purification process, relative to the original culture volume. High yield means greater than 1%, or more preferably greater than 5%, or higher yield. High yield means greater than 1 mg/ml, or more preferably greater than 3 mg/ml, or greater than 5 mg/ml, or higher yield.

TCRs of the invention preferably have a $K_D$ for the SLLQHLIGL (SEQ ID NO: 1)-HLA-A*02 complex of greater than (i.e. stronger than) the non-mutated, or scaffold TCR, for example in the range of 1 μM to 100 μM. In one aspect, TCRs of the invention have a $K_D$ for the complex of from about (i.e. +/−10%) 1 μM to about 400 nM, from about 1 μM to about 1000 μM, from about 1 μM to about 500 μM. Said TCRs may additionally, or alternatively, have a binding half-life (T ½) for the complex in the range of from about 1 min to about 60 h, from about 20 min to about 50 h, or from about 2 h to about 35 h. In a particularly preferred embodiment, TCRs of the invention have a $K_D$ for the SLLQHLIGL (SEQ ID NO: 1)-HLA-A*02 complex of from about 1 μM to about 500 μM and/or a binding half-life from about 2 h to about 35 h. Such high-affinity is preferable for TCRs in soluble format when associated with therapeutic agents and/or detectable labels.

In another aspect, TCRs of the invention may have a $K_D$ for the complex of from about 50 nM to about 200 μM, or from about 100 nM to about 1 μM and/or a binding half-life for the complex of from about 3 sec to about 12 min. Such TCRs may be preferable for adoptive therapy applications.

Methods to determine binding affinity (inversely proportional to the equilibrium constant $K_D$) and binding half life (expressed as T½) are known to those skilled in the art. In a preferred embodiment, binding affinity and binding half-life are determined using Surface Plasmon Resonance (SPR) or Bio-Layer Interferometry (BLI), for example using a BIAcore instrument or Octet instrument, respectively. A preferred method is provided in Example 3. It will be appreciated that doubling the affinity of a TCR results in halving the $K_D$. T½ is calculated as In2 divided by the off-rate ($k_{off}$). Therefore, doubling of T½ results in a halving in $k_{off}$. $K_D$ and $k_{off}$ values for TCRs are usually measured for soluble forms of the TCR, i.e. those forms which are truncated to remove cytoplasmic and transmembrane domain residues. To account for variation between independent measurements, and particularly for interactions with dissociation times in excess of 20 hours, the binding affinity and or binding half-life of a given TCR may be measured several times, for example 3 or more times, using the same assay protocol, and an average of the results taken. To compare binding data between two samples (i.e. two different TCRs and or two preparations of the same TCR) it is preferable that measurements are made using the same assay conditions (e.g. temperature), such as those described in Example 3.

Certain preferred TCRs of the invention have a binding affinity for, and/or a binding half-life for, the SLLQHLIGL (SEQ ID NO: 1)-HLA-A*02 complex that is substantially higher than that of the native TCR. Increasing the binding affinity of a native TCR often reduces the specificity of the TCR for its peptide-MHC ligand, and this is demonstrated in Zhao et al., (2007) J. Immunol, 179:9, 5845-5854. However, such TCRs of the invention remain specific for the SLLQHLIGL (SEQ ID NO: 1)-HLA-A*02 complex, despite having substantially higher binding affinity than the native TCR.

Certain preferred TCRs are able to generate a highly potent T cell response in vitro against antigen positive cells, in particular those cells presenting low levels of antigen typical of cancer cells (i.e. in the order of 5-100, for example 50, antigens per cell (Bossi et al., (2013) Oncoimmunol. 1; 2 (11):e26840; Purbhoo et al., (2006). J Immunol 176(12): 7308-7316.)). Such TCRs may be in soluble form and linked to an immune effector such as an anti-CD3 antibody. The T cell response that is measured may be the release of T cell activation markers such as Interferon γ or Granzyme B, or target cell killing, or other measure of T cell activation, such as T cell proliferation. Preferably a highly potent response is one with $EC_{50}$ value in the pM range, most preferably, 100 μM or lower.

TCRs of the invention may be αβ heterodimers. Alpha-beta heterodimeric TCRs of the invention usually comprise an alpha chain TRAC constant domain sequence and/or a beta chain TRBC1 or TRBC2 constant domain sequence. The constant domains may be full-length by which it is meant that extracellular, transmembrane and cytoplasmic domains are present, or they may be in soluble format (i.e. having no transmembrane or cytoplasmic domains). One or both of the constant domains may contain mutations, substitutions or deletions relative to the native TRAC and/or TRBC½ sequences. The term TRAC and TRBC½ also encompasses natural polymorphic variants, for example N to K at position 4 of TRAC (Bragado et al International immunology. 1994 February; 6(2):223-30).

For soluble TCRs of the invention, the alpha and beta chain constant domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may have an introduced disulphide bond between residues of the respective constant domains, as described, for example, in WO03/020763. In a preferred embodiment the alpha and beta constant domains may be modified by substitution of cysteine residues at position Thr 48 of TRAC and position Ser 57 of TRBC1 or TRBC2, the said cysteines forming a disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. One or both of the extracellular constant domains present in an αβ heterodimer of the invention may be truncated at the C terminus or C termini, for example by up to 15, or up to 10, or up to 8 or fewer amino acids. One or both of the extracellular constant domains present in an αβ heterodimer of the invention may be truncated at the C terminus or C termini by, for example, up to 15, or up to 10 or up to 8 amino acids. The C terminus of the alpha chain extracellular constant domain may be truncated by 8 amino acids. Soluble TCRs are preferably associated with therapeutic agents and/or detectable labels The constant domains of an αβ heterodimeric TCR may be full length, having both transmembrane and cytoplasmic domains. Such TCRs may contain a disulphide bond corresponding to that found in nature between the respective alpha and beta constant domains. Additionally, or alternatively, a non-native disulphide bond may be present between the extracellular constant domains. Said non-native disulphide bonds are further described in WO03020763 and WO06000830. The non-native disulphide bond may be between position Thr 48 of TRAC and position Ser 57 of TRBC1 or TRBC2. One or both of the constant domains may contain one or more mutations substitutions or deletions relative to the native TRAC and/or TRBC½ sequences. TCRs with full-length constant domains are preferable for use in adoptive therapy.

TCRs of the invention may be in single chain format. Single chain formats include, but are not limited to, αβ TCR polypeptides of the Vα-L-Vβ, Vβ-L-Vα, Vα-Cα-L-Vβ, Vα-L-Vβ-Cβ, or Vα-Cα-L-Vβ-Cβ types, wherein Vα and Vβ are TCR α and β variable regions respectively, Cα and Cβ are TCR α and β constant regions respectively, and L is a linker sequence (Weidanz et al., (1998) J Immunol Methods. December 1; 221(1-2):59-76; Epel et al., (2002), Cancer Immunol Immunother. November; 51(10):565-73; WO 2004/033685; WO9918129). Where present, one or both of the constant domains may be full length, or they may be truncated and/or contain mutations as described above. Preferably single chain TCRs are soluble. In certain embodiments single chain TCRs of the invention may have an introduced disulphide bond between residues of the respective constant domains, as described in WO 2004/033685. Single chain TCRs are further described in WO2004/ 033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

The invention also includes particles displaying TCRs of the invention and the inclusion of said particles within a library of particles. Such particles include but are not limited to phage, yeast cells, ribosomes, or mammalian cells. Method of producing such particles and libraries are known in the art (for example see WO2004/044004; WO01/48145, Chervin et al. (2008) J. Immuno. Methods 339.2: 175-184).

Soluble TCRs of the invention are useful for delivering detectable labels or therapeutic agents to antigen presenting cells and tissues containing antigen presenting cells. They may therefore be associated (covalently or otherwise) with a detectable label (for diagnostic purposes wherein the TCR is used to detect the presence of cells presenting the cognate antigen); and or a therapeutic agent; and or a PK modifying moiety.

Examples of PK modifying moieties include, but are not limited to, PEG (Dozier et al., (2015) Int J Mol Sci. October 28; 16(10):25831-64 and Jevsevar et al., (2010) Biotechnol J. January; 5(1):113-28), PASylation (Schlapschy et al., (2013) Protein Eng Des Sel. August; 26(8):489-501), albumin, and albumin binding domains, (Dennis et al., (2002) J Biol Chem. September 20; 277(38):35035-43), and/or unstructured polypeptides (Schellenberger et al., (2009) Nat Biotechnol. December; 27(12):1186-90). Further PK modifying moieties include antibody Fc fragments.

Detectable labels for diagnostic purposes include for instance, fluorescent labels, radiolabels, enzymes, nucleic acid probes and contrast reagents.

For some purposes, the TCRs of the invention may be aggregated into a complex comprising several TCRs to form a multivalent TCR complex. There are a number of human proteins that contain a multimerisation domain that may be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent TCR complex of the invention may have enhanced binding capability for the complex compared to a non-multimeric wild-type or T cell receptor heterodimer of the invention. Thus, multivalent complexes of TCRs of the invention are also included within the invention. Such multivalent TCR complexes according to the invention are particularly useful for tracking or targeting cells presenting particular antigens in vitro or in vivo, and are also useful as intermediates for the production of further multivalent TCR complexes having such uses.

Therapeutic agents which may be associated with the TCRs of the invention include immune-modulators and effectors, radioactive compounds, enzymes (perforin for example) or chemotherapeutic agents (cis-platin for example). To ensure that toxic effects are exercised in the desired location the toxin could be inside a liposome linked to TCR so that the compound is released slowly. This will prevent damaging effects during the transport in the body and ensure that the toxin has maximum effect after binding of the TCR to the relevant antigen presenting cells.

Examples of suitable therapeutic agents include, but are not limited to:

small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate 21arbour2late, auristatin E vincristine and doxorubicin;

peptide cytotoxins, i.e. proteins or fragments thereof with the ability to kill mammalian cells. For example, ricin, diphtheria toxin, *pseudomonas* bacterial exotoxin A, Dnase and Rnase;

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

Immuno-stimulants, i.e. immune effector molecules which stimulate immune response. For example, cytokines such as IL-2 and IFN-γ, Superantigens and mutants thereof;

TCR-HLA fusions, e.g. fusion to a peptide-HLA complex, wherein said peptide is derived from a common human pathogen, such as Epstein Barr Virus (EBV);

chemokines such as IL-8, platelet factor 4, melanoma growth stimulatory protein, etc;

antibodies or fragments thereof, including anti-T cell or NK cell determinant antibodies (e.g. anti-CD3, anti-CD28 or anti-CD16);

alternative protein scaffolds with antibody like binding characteristics complement activators;

xenogeneic protein domains, allogeneic protein domains, viral/bacterial protein domains, viral/bacterial peptides.

One preferred embodiment is provided by a soluble TCR of the invention associated (usually by fusion to the N— or C-terminus of the alpha or beta chain) with an immune effector. A particularly preferred immune effector is an anti-CD3 antibody, or a functional fragment or variant of said anti-CD3 antibody (such TCR-anti-CD3 fusions may be termed ImmTAC™ molecules). As used herein, the term "antibody" encompasses such fragments and variants. Examples of anti-CD3 antibodies include but are not limited to OKT3, UCHT-1, BMA-031 and 12F6. Antibody fragments and variants/analogues which are suitable for use in the compositions and methods described herein include minibodies, Fab fragments, F(ab')$_2$ fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (*Pieris* (Germany)), comprising engineered anticalins) to name but a few.

Linkage of the TCR and the anti-CD3 antibody may be via covalent or non-covalent attachment. Covalent attachment may be direct, or indirect via a linker sequence. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. Examples of suitable linkers that may be used in TCRs of the invention include, but are not limited to: GGGGS (SEQ ID NO: 31), GGGSG (SEQ ID NO: 32), GGSGG (SEQ ID NO: 33), GSGGG (SEQ ID NO: 34), GSGGGP (SEQ ID NO: 35), GGEPS (SEQ ID NO: 36), GGEGGGP (SEQ ID NO: 37), and GGEGGGSEGGGS (SEQ ID NO: 38) (as described in WO2010/133828).

Specific embodiments of anti-CD3-TCR fusion constructs of the invention include those alpha and beta chain pairings in which the alpha chain is composed of a TCR variable domain comprising the amino acid sequence of SEQ ID NOs: 6-8 and/or the beta chain is composed of a TCR variable domain comprising the amino acid sequence of SEQ ID NOs: 9-24. Said alpha and beta chains may further comprise a constant region comprising a non-native disulphide bond. The constant domain of the alpha chain may be truncated by eight amino acids. The N or C terminus of the alpha and or beta chain may be fused to an anti-CD3 scFv antibody fragment via a linker selected from SEQ ID NOs: 31-38. Certain preferred embodiments of such anti-CD3-TCR fusion constructs are provided below:

| Alpha chain SEQ ID NO | Beta Chain SEQ ID NO |
|---|---|
| SEQ ID NO 25 | SEQ ID NO 26 |
| SEQ ID NO 27 | SEQ ID NO 28 |
| SEQ ID NO 29 | SEQ ID NO 30 |

Also included within the scope of the invention are functional variants of said anti-CD3-TCR fusion constructs. Said functional variants preferably have at least 90% identity, such as 90%, 91%, 92%, 93%, 94%, 95%, 96%, 97%, 98%, 99% or 100% identity to the reference sequence, but are nonetheless functionally equivalent.

In a further aspect, the present invention provides nucleic acid encoding a TCR, or TCR anti-CD3 fusion of the invention. In some embodiments, the nucleic acid is cDNA. In some embodiments the nucleic acid may be mRNA. In some embodiments, the invention provides nucleic acid comprising a sequence encoding an α chain variable domain of a TCR of the invention. In some embodiments, the invention provides nucleic acid comprising a sequence encoding a p chain variable domain of a TCR of the invention. The nucleic acid may be non-naturally occurring and/or purified and/or engineered. The nucleic acid sequence may be codon optimised, in accordance with expression system utilised. As is known to those skilled in the art, expression systems may include bacterial cells such as *E. coli*, or yeast cells, or mammalian cells, or insect cells, or they may be cell free expression systems.

In another aspect, the invention provides a vector which comprises nucleic acid of the invention. Preferably the vector is a TCR expression vector. Suitable TCR expression vectors include, for example, gamma-retroviral vectors or, more preferably, lentiviral vectors. Further details can be found in Zhang 2012 and references therein (Zhang et al, Adv Drug Deliv Rev. 2012 Jun. 1; 64(8): 756-762).

The invention also provides a cell harbouring a vector of the invention, preferably a TCR expression vector. Suitable cells include, mammalian cells, preferably immune cells, even more preferably T cells. The vector may comprise nucleic acid of the invention encoding in a single open reading frame, or two distinct open reading frames, encoding the alpha chain and the beta chain respectively. Another aspect provides a cell harbouring a first expression vector which comprises nucleic acid encoding the alpha chain of a TCR of the invention, and a second expression vector which comprises nucleic acid encoding the beta chain of a TCR of the invention. Such cells are particularly useful in adoptive therapy. The cells of the invention may be isolated and/or recombinant and/or non-naturally occurring and/or engineered.

Since the TCRs of the invention have utility in adoptive therapy, the invention includes a non-naturally occurring and/or purified and/or or engineered cell, especially a T-cell, presenting a TCR of the invention. The invention also provides an expanded population of T cells presenting a TCR of the invention. There are a number of methods suitable for the transfection of T cells with nucleic acid (such as DNA, cDNA or RNA) encoding the TCRs of the invention (see for example Robbins et al., (2008) J Immunol. 180: 6116-6131). T cells expressing the TCRs of the invention will be suitable for use in adoptive therapy-based treatment of cancer. As will be known to those skilled in the art, there are a number of suitable methods by which adoptive therapy can be carried out (see for example Rosenberg et al., (2008) Nat Rev Cancer 8(4): 299-308).

As is well-known in the art, TCRs may be subject to post translational modifications. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis et al., (2009) Nat Rev Drug Discov March; 8(3):226-34.). For soluble TCRs of the invention glycosylation may be controlled, by using particular cell lines for example (including but not limited to mammalian cell lines such as Chinese hamster ovary (CHO) cells or human embryonic kidney (HEK) cells), or by chemical modification. Such modifications may be desirable, since glycosylation can improve pharmacokinetics, reduce immunogenicity and more closely mimic a native human protein (Sinclair and Elliott, (2005) Pharm Sci.August; 94(8):1626-35).

For administration to patients, the TCRs of the invention (preferably associated with a detectable label or therapeutic agent or expressed on a transfected T cell), TCR-anti CD3 fusion molecules, nucleic acids, expression vectors or cells of the invention may be provided as part of a sterile pharmaceutical composition together with one or more pharmaceutically acceptable carriers or excipients. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, intrathecal or intravenous), enteral (including oral or rectal), inhalation or intranasal routes. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. a suitable dose range for a TCR-anti-CD3 fusion molecules may be in the range of 25 ng/kg to 50 pg/kg or 1 pg to 1 g. A physician will ultimately determine appropriate dosages to be used.

TCRs, TCR-anti-CD3 fusion molecules, pharmaceutical compositions, vectors, nucleic acids and cells of the invention may be provided in substantially pure form, for example, at least 80%, at least 85%, at least 90%, at least 91%, at least 92%, at least 93%, at least 94%, at least 95%, at least 96%, at least 97%, at least 98%, at least 99% or 100% pure.

Also provided by the invention are:
A TCR, TCR-anti-CD3 fusion molecule, nucleic acid, pharmaceutical composition or cell of the invention for use in medicine, preferably for use in a method of treating cancer or a tumour;
the use of a TCR, TCR-anti-CD3 fusion molecule, nucleic acid, pharmaceutical composition or cell of the invention in the manufacture of a medicament for treating cancer or a tumour;
a method of treating cancer or a tumour in a patient, comprising administering to the patient a TCR, TCR-anti-CD3 fusion molecule, nucleic acid, pharmaceutical composition or cell of the invention;
an injectable formulation for administering to a human subject comprising a TCR, TCR-anti-CD3 fusion molecule, nucleic acid, pharmaceutical composition or cell of the invention.

The cancer may be a solid or liquid tumour. Preferable the tumour expresses PRAME. The cancer may be of the breast (including triple negative), ovary, endometrium, oesophagus, lung (NSCLC and SCLC), bladder or the head and neck. Alternatively or additionally the cancer may be a leukemia or lymphoma. Of these cancers, breast (including triple negative), ovary and endometrium are preferred. The TCR, TCR-anti-CD3 fusion molecule, nucleic acid, pharmaceutical composition or cell of the invention may be administered by injection, such as intravenous or direct intratumoral injection. The human subject may be of the HLA-A*02 subtype.

The method of treatment may further include administering separately, in combination, or sequentially, an additional anti-neoplastic agent. Example of such agents are known in the art and may include immune activating agents and/or T cell modulating agents.

Preferred features of each aspect of the invention are as for each of the other aspects mutatis mutandis. The prior art documents mentioned herein are incorporated by reference to the fullest extent permitted by law.

DESCRIPTION OF THE DRAWINGS

FIG. 1—provides the amino acid sequence of the extracellular regions of the scaffold PRAME TCR alpha and beta chain.

FIG. 2—provides the amino acid sequence of the extracellular regions of a soluble version of the scaffold PRAME TCR alpha and beta chain.

FIG. 3—provides example amino acid sequences of mutated PRAME TCR alpha chain variable regions.

FIG. 4—provides example amino acid sequences of mutated PRAME TCR beta chain variable regions.

FIG. 5—provides amino acid sequences of ImmTAC molecules (TCR-anti-CD3 fusions) comprising certain mutated PRAME TCR variable domains as set out in FIGS. 3 and 4.

FIG. 8—provides cellular data demonstrating killing of PRAME positive melanoma cancer cells by ImmTAC molecules of FIG. 5, comprising the mutated PRAME TCR variable domains as set out in FIGS. 3 and 4.

FIG. 9—provides cellular data demonstrating killing of PRAME positive lung cancer cells by ImmTAC molecules of FIG. 5, comprising the mutated PRAME TCR variable domains as set out in FIGS. 3 and 4.

Figure 6:
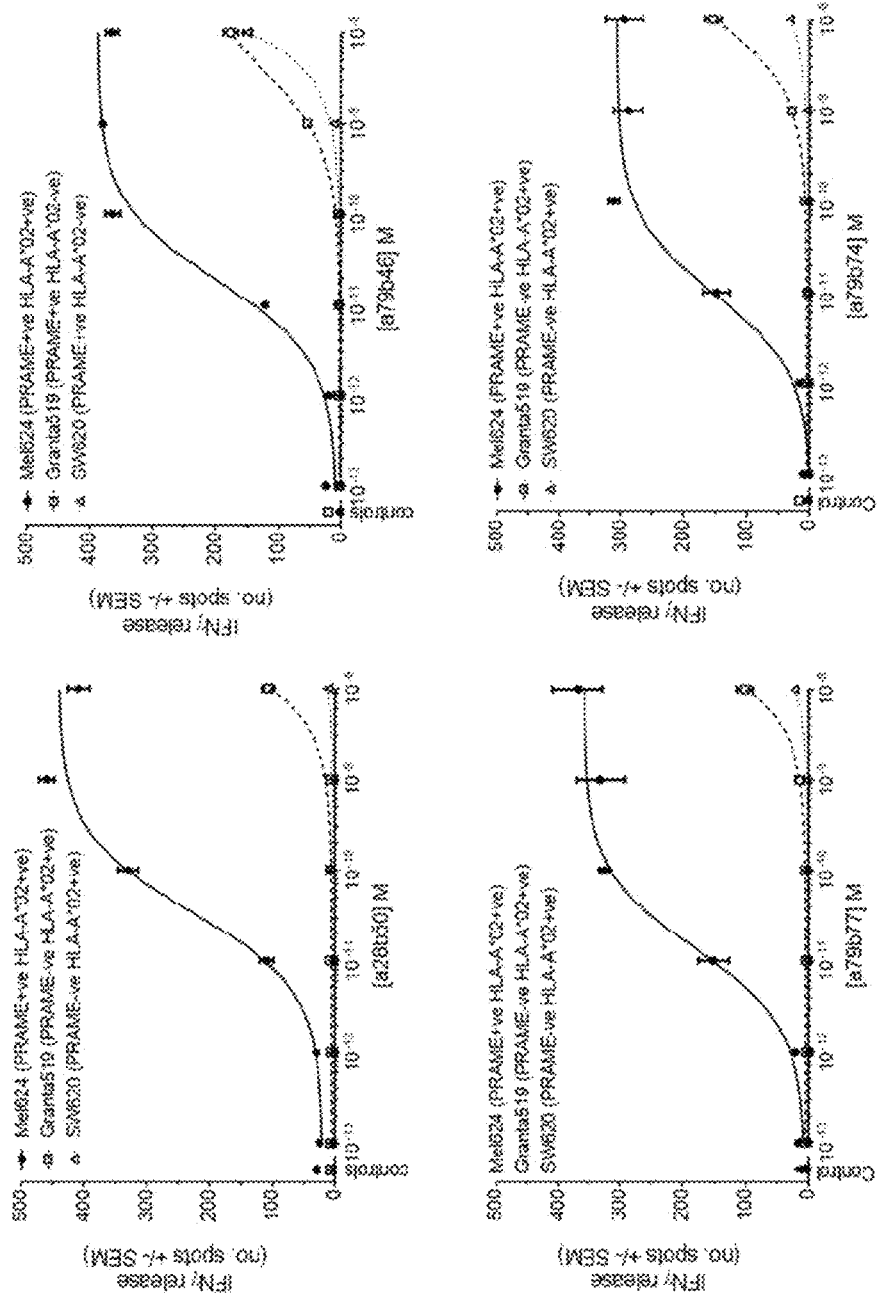
FIG. 6—provides cellular data demonstrating potency and specificity of ImmTAC molecules of FIG. 5 comprising the mutated PRAME TCR variable domains as set out in FIGS. 3 and 4.

The invention is further described in the following non-limiting examples.

Examples

Example 1—Expression, Refolding and Purification of Soluble TCRs

Method

DNA sequences encoding the alpha and beta extracellular regions of soluble TCRs of the invention were cloned separately into pGMT7-based expression plasmids using standard methods (as described in Sambrook, et al. *Molecular cloning*. Vol. 2. (1989) New York: Cold spring harbour laboratory press). The expression plasmids were transformed separately into *E. coli* strain Rosetta (BL21 pLysS), or T7 Express, and single ampicillin-resistant colonies were grown at 37° C. in TYP (+ampicillin 100 µg/ml) medium to an $OD_{600}$ of ~0.6-0.8 before inducing protein expression with 0.5 mM IPTG. Cells were harvested three hours post-induction by centrifugation. Cell pellets were lysed with BugBuster protein extraction reagent (Merck Millipore) according to the manufacturer's instructions. Inclusion body pellets were recovered by centrifugation. Pellets were washed twice in Triton buffer (50 mM Tris-HCl pH 8.1, 0.5% Triton-X100, 100 mM NaCl, 10 mM NaEDTA) and finally resuspended in detergent free buffer (50 mM Tris-HCl pH 8.1, 100 mM NaCl, 10 mM NaEDTA). Inclusion body protein yield was quantified by solubilising with 6 M guanidine-HCl and measuring $OD_{280}$. Protein concentration was then calculated using the extinction coefficient. Inclusion body purity was measured by solubilising with 8M Urea and loading ~2 µg onto 4-20% SDS-PAGE under reducing conditions. Purity was then estimated or calculated using densitometry software (Chemidoc, Biorad). Inclusion bodies were stored at +4° C. for short term storage and at −20° C. or −70° C. for longer term storage.

For soluble TCR refolding, a and 3 chain-containing inclusion bodies were first mixed and diluted into 10 ml solubilisation/denaturation buffer (6 M Guanidine-hydrochloride, 50 mM Tris HCl pH 8.1, 100 mM NaCl, 10 mM EDTA, 20 mM DTT) followed by incubation for 30 min at 37° C. Refolding was then initiated by further dilution into 1 L of refold buffer (100 mM Tris pH 8.1, 800 or 1000 mM L-Arginine HCL, 2 mM EDTA, 4 M Urea, 10 mM cysteamine hydrochloride and 2.5 mM cystamine dihydrochloride) and the solution mixed well. The refolded mixture was dialysed against 10 L $H_2O$ for 18-20 hours at 5° C.±3° C. After this time, the dialysis buffer was twice replaced with 10 mM Tris pH 8.1 (10 L) and dialysis continued for another 15 hours. The refold mixture was then filtered through 0.45 µm cellulose filters.

Purification of soluble TCRs was initiated by applying the dialysed refold onto a POROS® 50HQ anion exchange column and eluting bound protein with a gradient of 0-500 mM NaCl in 20 mM Tris pH 8.1 over 6 column volumes using an Akta® Pure (GE Healthcare). Peak TCR fractions were identified by SDS PAGE before being pooled and concentrated. The concentrated sample was then applied to a Superdex® 200 Increase 10/300 GL gel filtration column (GE Healthcare) pre-equilibrated in Dulbecco's PBS buffer. The peak TCR fractions were pooled and concentrated and the final yield of purified material calculated.

Example 2—Expression, Refolding and Purification of ImmTAC Molecules (Soluble TCR-Anti CD3 Fusion Molecules)

Method

ImmTAC preparation was carried out as described in Example 1, except that the TCR beta chain was fused via a linker to an anti-CD3 single chain antibody. In addition a cation exchange step was performed during purification following the anion exchange. In this case the peak fractions from anion exchange were diluted 20-fold in 20 mM MES (pH6.5), and applied to a POROS® 50HS cation exchange column. Bound protein was eluted with a gradient of 0-500 mM NaCl in 20 mM MES. Peak ImmTAC fractions were pooled and adjusted to 50 mM Tris pH 8.1, before being concentrated and applied directly to the gel filtration matrix as described in Example 1.

Example 3—Binding Characterisation

Binding analysis of purified soluble TCRs and ImmTAC molecules to the relevant peptide-HLA complex was carried out by surface plasmon resonance, using a BIAcore 3000 or BIAcore T200 instrument, or by biolayer interferometry, using a ForteBio Octet instrument). Biotinylated class I HLA-A*02 molecules were refolded with the peptide of interest and purified using methods known to those in the art (O'Callaghan et al. (1999). Anal Biochem 266(1): 9-15; Garboczi, et al. (1992). Proc Natl Acad Sci USA 89(8): 3429-3433). All measurements were performed at 25° C. in Dulbecco's PBS buffer, supplemented with 0.005% P20.

BIAcore method

Biotinylated peptide-HLA monomers were immobilized on to streptavidin-coupled CM-5 sensor chips. Equilibrium binding constants were determined using serial dilutions of soluble TCR/ImmTAC injected at a constant flow rate of 30 µl $min^{-1}$ over a flow cell coated with ~200 response units (RU) of peptide-HLA-A*02 complex. Equilibrium responses were normalised for each TCR concentration by subtracting the bulk buffer response on a control flow cell containing an irrelevant peptide-HLA. The $K_D$ value was obtained by non-linear curve fitting using Prism software and the Langmuir binding isotherm, bound=C*Max/(C+$K_D$), where "bound" is the equilibrium binding in RU at injected TCR concentration C and Max is the maximum binding.

For high affinity interactions, binding parameters were determined by single cycle kinetics analysis. Five different concentrations of soluble TCR/ImmTAC were injected over a flow cell coated with ~100-200 RU of peptide-HLA complex using a flow rate of 50-60 µl $min^{-1}$. Typically, 60-120 µl of soluble TCR/ImmTAC was injected at a top concentration of between 50-100 nM, with successive 2 fold dilutions used for the other four injections. The lowest concentration was injected first. To measure the dissociation phase buffer was then injected until 10% dissociation occurred, typically after 1-3 hours. Kinetic parameters were calculated using BIAevaluation® software. The dissociation phase was fitted to a single exponential decay equation enabling calculation of half-life. The equilibrium constant $K_D$ was calculated from $k_{off}/k_{on}$.

Octet Method

Biotinylated peptide-HLA monomers were captured to 1 nm on to (SA) streptavidin biosensors (Pall ForteBio) pre-immobilised with streptavidin. The sensors were blocked with free biotin (2 μM) for 2 minutes. Equilibrium binding constants were determined by immersing the loaded biosensors into soluble TCR/ImmTAC serially diluted in a 96-well or 384-well sample plate. Plate shaking was set to 1000 rpm. For low affinity interactions (μM range) a short association (~2 minutes) and a short dissociation time (~2 minutes) was used. Binding curves were processed by double reference subtraction of reference biosensors loaded with irrelevant pHLA using Octet Data Analysis Software (Pall ForteBio). Responses (nm) at equilibrium were used to estimate the $K_D$ value from steady state plots fitted to the equation Response=Rmax*conc/($K_D$+conc), where "response" is the equilibrium binding in nm at each TCR concentration (conc) and Rmax is the maximum binding response at pHLA saturation.

For high affinity interactions (nM-pM range), kinetic parameters were determined from binding curves at ≥3 TCR/ImmTAC concentrations typically 10 nM, 5 nM and 2.5 nM. The association time was 30 minutes and the dissociation time 1-2 hours. Binding curves were processed by double reference subtraction of reference biosensors loaded with irrelevant pHLA and blocked with biotin. Kinetic parameters $k_{on}$ and $k_{off}$ were calculated by global fitting directly to the binding curves using Octet Data Analysis Software (Pall ForteBio). $K_D$ was calculated from $k_{off}/k_{on}$ and the dissociation half-life was calculated from $t_{1/2}=0.693/k_{off}$.

Example 4—Binding Characterisation of the Native TCR

A soluble native TCR was prepared according to the methods described in Example 1 and binding to pHLA analysed according to Example 3. The amino acid sequences of the alpha and beta chains corresponded to those shown in FIG. 2. Soluble biotinylated HLA-A*02 was prepared with the PRAME peptide SLLQHLIGL (SEQ ID NO: 1) and immobilised onto a BIAcore sensor chip.

Results

Binding was determined at various concentrations and the $K_D$ value for the interaction was determined to be 141 μM. Cross reactivity (specificity) was assessed against a panel of 14 irrelevant peptide HLA-A*02 complexes using the equilibrium BIAcore method of Example 3. The 14 irrelevant pHLAs were divided into three groups and loaded onto one of three flow cells, to give approximately 1000 RU of each pHLA per flow cell. 30 μL of soluble wild type TCR was injected at concentrations of 130 and 488 μM over all flow cells at a rate of 20 μL/min. No significant binding was detected at either concentration indicting that the native TCR is specific for the SLLQHLIGL (SEQ ID NO: 1)-HLA-A*02 complex.

These data indicate that this native TCR has characteristics that are suitable for use as a starting sequence for engineering high affinity therapeutic TCRs.

Example 5—Binding Characterisation of Certain Mutated TCRs of the Invention

The mutated TCR alpha and beta variable domain amino acid sequences, provided in FIGS. 3 and 4 respectively (SEQ ID NOs: 6-24), were used to prepare ImmTAC molecules. Note that inclusion of a glycine residue at the start of the alpha chain (~1 position relative to the numbering of SEQ ID NO: 2) was found to improve cleavage efficiency of the N terminal methionine during production in *E. coli*. Inefficient cleavage may be detrimental for a therapeutic since it may result in a heterogeneous protein product and or the presence of the initiation methionine may be immunogenic in humans. Full amino acid sequences of ImmTAC molecules comprising the following alpha and beta chains are provided in FIG. 5 a28b50—ImmTAC1
a79b74—ImmTAC2
a79b46—ImmTAC3

The molecules were prepared as described in Example 2 and binding to SLLQHLIGL (SEQ ID NO: 1)-HLA-A*02 complex was determined according to Example 3.

Results

The data presented in the table below show that ImmTAC molecules comprising the indicated TCR variable domain sequences recognised SLLQHLIGL (SEQ ID NO: 1)-HLA-A*02 complex with a particularly suitable affinity and/or half-life.

| α chain | β chain | $k_D$ | $t_{1/2}$ |
|---|---|---|---|
| a28 (SEQ ID NO: 6) | b50 (SEQ ID NO: 9) | 391 pM | 1.8 h |
| a28 (SEQ ID NO: 6) | b60 (SEQ ID NO: 19) | 261 pM | 2.8 h |
| a28 (SEQ ID NO: 6) | b74 (SEQ ID NO: 17) | 182 pM | 3.7 h |
| a28 (SEQ ID NO: 6) | b75 (SEQ ID NO: 20) | 214 pM | 5.1 h |
| a28 (SEQ ID NO: 6) | b57 (SEQ ID NO: 10) | 83 pM | 8.3 h |
| a28 (SEQ ID NO: 6) | b58 (SEQ ID NO: 21) | 79 pM | 8.9 h |
| a79 (SEQ ID NO: 7) | b46 (SEQ ID NO: 11) | 31.8 pM | 29.2 h |
| a109 (SEQ ID NO: 8) | b46 (SEQ ID NO: 11) | 170 pM | 7.31 h |
| a79 (SEQ ID NO: 7) | b63 (SEQ ID NO: 22) | 79 pM | 10.8 h |
| a79 (SEQ ID NO: 7) | b64 (SEQ ID NO: 12) | 138 pM | 6.38 h |
| a79 (SEQ ID NO: 7) | b66 (SEQ ID NO: 23) | 89 pM | 9.16 h |
| a79 (SEQ ID NO: 7) | b67 (SEQ ID NO: 13) | 47 pM | 12.69 h |
| a79 (SEQ ID NO: 7) | b69 (SEQ ID NO: 14) | 52 pM | 20.41 h |
| a79 (SEQ ID NO: 7) | b71 (SEQ ID NO: 15) | 87 pM | 14.89 h |
| a79 (SEQ ID NO: 7) | b58 (SEQ ID NO: 21) | 23.1 pM | 28.7 h |
| a79 (SEQ ID NO: 7) | b73 (SEQ ID NO: 16) | 132 pM | 4.6 h |
| a79 (SEQ ID NO: 7) | b74 (SEQ ID NO: 17) | 53.3 pM | 12.5 h |
| a79 (SEQ ID NO: 7) | b75 (SEQ ID NO: 20) | 57.7 pM | 16.9 h |
| a79 (SEQ ID NO: 7) | b76 (SEQ ID NO: 24) | 11.8 pM | 58.3 h |
| a79 (SEQ ID NO: 7) | b77 (SEQ ID NO: 18) | 77.9 pM | 8.6 h |

Example 6-Potency and Specificity Characterisation of Certain Mutated TCRs of the Invention ImmTAC molecules comprising the same TCR variable domain sequences as set out in Example 5 were assessed for their ability to mediate potent and specific redirection of CD3+ T cells against PRAME positive cancer cells. Interferon-γ (IFN-γ) release was used as a read out for T cell activation.

Full amino acid sequences of ImmTAC molecules comprising the following alpha and beta chains are provided in FIG. 5 a28b50—ImmTAC1
a79b74—ImmTAC2
a79b46—ImmTAC3

Assays were performed using a human IFN-γ ELISPOT kit (BD Biosciences) according to the manufacturers instructions. Briefly, target cells were prepared at a density of 1×10⁶/ml in assay medium (RPMI 1640 containing 10% heat inactivated FBS and 1% penicillin-streptomycin-L-glutamine) and plated at 50,000 cells per well in a volume of 50 μl. Peripheral blood mononuclear cells (PBMC), isolated from fresh donor blood, were used as effector cells and plated at 50,000 cells per well in a volume of 50 μl (the exact number of cells used for each experiment is donor dependent and may be adjusted to produce a response within a suitable range for the assay). ImmTAC molecules were titrated to give final concentrations of 10 nM, 1 nM, 0.1 nM, 0.01 nM and 0.001 nM, spanning the anticipated clinically relevant range, and added to the well in a volume of 50 μl.

Plates were prepared according to the manufacturer's instructions. Target cells, effector cells and ImmTAC molecules were added to the relevant wells and made up to a final volume of 200 μl with assay medium. All reactions were performed in triplicate. Control wells were also prepared with the omission of, ImmTAC, effector cells, or target cells. The plates were then incubated overnight (37° C./5% $CO_2$). The next day the plates were washed three times with wash buffer (1×PBS sachet, containing 0.05% Tween-20, made up in deionised water). Primary detection antibody was then added to each well in a volume of 50 μl. Plates were incubated at room temperature for 2 hours prior to being washed again three times. Secondary detection was performed by adding 50 μl of diluted streptavidin-HRP to each well and incubating at room temperature for 1 hour and the washing step repeated. No more than 15 mins prior to use, one drop (20 μl) of AEC chromogen was added to each 1 ml of AEC substrate and mixed and 50 μl added to each well. Spot development was monitored regularly and plates were washed in tap water to terminate the development reaction. The plates were then allowed to dry at room temperature for at least 2 hours prior to counting the spots using a CTL analyser with Immunospot software (Cellular Technology Limited).

In this example, the following cancer cells lines were used as target cells:
  Me1624 (melanoma) PRAME+ve HLA-A*02+ve
  Granta519 (hemo-lymphocytic) PRAME-ve HLA-A*02+ve
  SW620 (colon carcinoma) PRAME-ve HLA-A*02+ve
  HT144 (melanoma) PRAME+ve HLA-A*02-ve
  Results Each of the ImmTAC molecules, comprising the alpha and beta variable domains indicated in the table below, demonstrated potent activation of redirected T cells in the presence of antigen positive Me1624 cells. In each case, EC50 values were calculated from the data and are shown in the table below. In addition, each ImmTAC molecule demonstrated minimal or no recognition of two antigen negative, HLA-A*02 positive cells, at a concentration of up to 1 nM. The ImmTAC molecules also demonstrated no recognition of PRAME positive cells that are HLA-A*02 negative (data not shown). FIG. 6 shows representative data from four of the ImmTAC molecules listed in the table below.

| α chain (SEQ ID NO) | β chain (SEQ ID NO) | $EC_{50}$ (mel624) |
|---|---|---|
| a28 (SEQ ID NO: 6) | b50 (SEQ ID NO: 9) | 34.8 pM |
| a28 (SEQ ID NO: 6) | b60 (SEQ ID NO: 19) | 31.7 pM |
| a28 (SEQ ID NO: 6) | b74 (SEQ ID NO: 17) | 24.3 pM |
| a28 (SEQ ID NO: 6) | b75 (SEQ ID NO: 20) | 13.9 pM |
| a28 (SEQ ID NO: 6) | b57 (SEQ ID NO: 10) | 13.4 pM |
| a28 (SEQ ID NO: 6) | b58 (SEQ ID NO: 21) | 12 pM |
| a79 (SEQ ID NO: 7) | b46 (SEQ ID NO: 11) | 18.6 pM |
| a109 (SEQ ID NO: 8) | b46 (SEQ ID NO: 11) | 60.1 pM |
| a79 (SEQ ID NO: 7) | b63 (SEQ ID NO: 22) | 22.9 pM |
| a79 (SEQ ID NO: 7) | b64 (SEQ ID NO: 12) | 27.5 pM |
| a79 (SEQ ID NO: 7) | b66 (SEQ ID NO: 23) | 16.7 pM |
| a79 (SEQ ID NO: 7) | b67 (SEQ ID NO: 13) | 26.3 pM |
| a79 (SEQ ID NO: 7) | b69 (SEQ ID NO: 14) | 39.8 pM |
| a79 (SEQ ID NO: 7) | b71 (SEQ ID NO: 15) | 31.8 pM |
| a79 (SEQ ID NO: 7) | b58 (SEQ ID NO: 21) | 10.6 pM |
| a79 (SEQ ID NO: 7) | b73 (SEQ ID NO: 16) | 23.1 pM |
| a79 (SEQ ID NO: 7) | b74 (SEQ ID NO: 17) | 9.55 pM |
| a79 (SEQ ID NO: 7) | b75 (SEQ ID NO: 20) | 23.6 pM |
| a79 (SEQ ID NO: 7) | b76 (SEQ ID NO: 24) | 17.2 pM |
| a79 (SEQ ID NO: 7) | b77 (SEQ ID NO: 18) | 13.8 pM |

These data demonstrate that ImmTAC molecules comprising mutated TCR variable domain sequences of the invention can mediate potent and specific T cell redirection against PRAME positive, HLA-A*02 positive, cancer cells, in a concentration range suitable for therapeutic use.

Example 7—Further Specificity Characterisation of Certain Mutated TCRs of the Invention To further demonstrate the specificity of ImmTAC molecules comprising the mutated TCR sequences, further testing was carried out using the same ELISPOT methodology as described in Example 6, with a panel of normal cells derived from healthy human tissues as target cells.

Normal tissues included cardiovascular, renal, skeletal muscle, pulmonary, vasculature, hepatic and brain. In each case antigen positive Me1624 cancer cells were used as a positive control.

The data presented in this example includes ImmTAC molecules comprising the following TCR alpha and beta chains
  a28b50
  a79b74
  a79b46
  a79b77

The full amino acid sequences of ImmTAC molecules comprising a28b50, a79b74 and a79b46 are provided in FIG. 5 (ImmTAC 1-3 respectively)

Results

Figure 7:
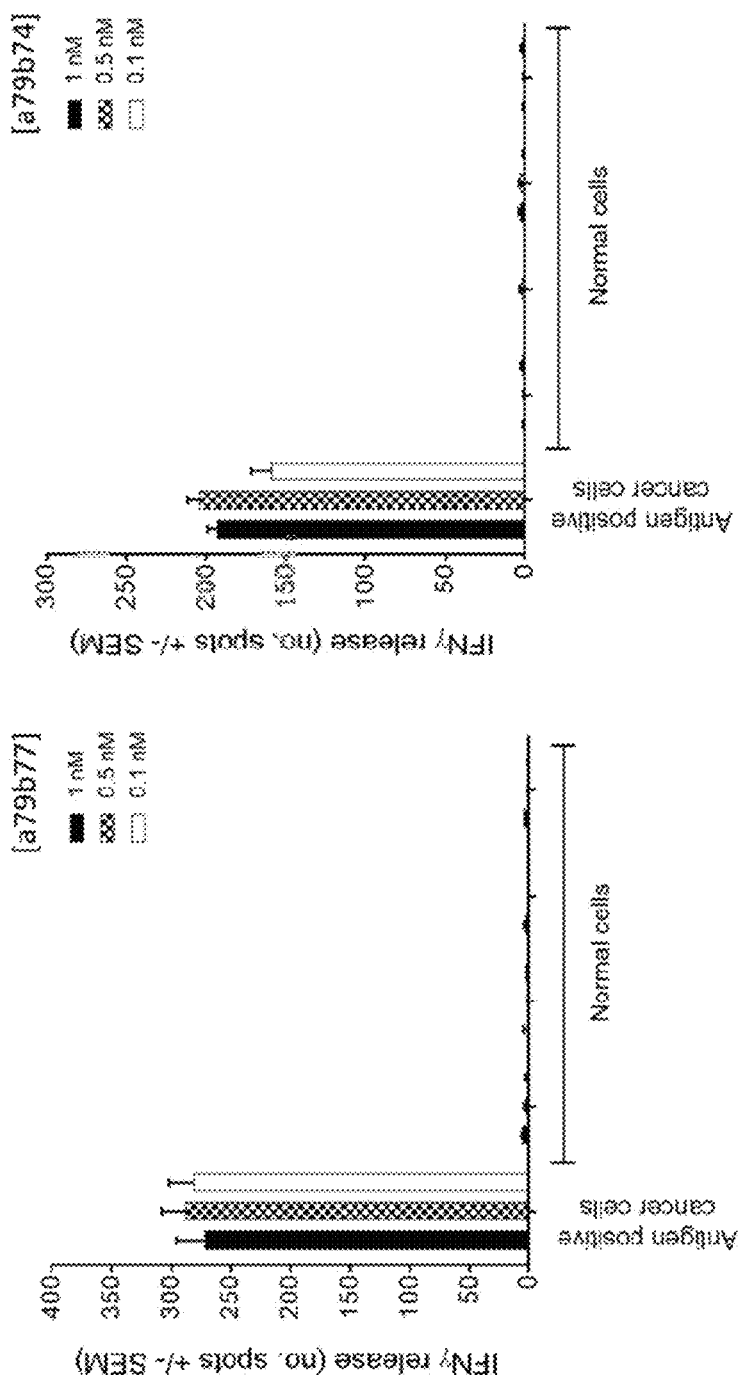
FIG. 7 (panels a and b)—provide cellular data demonstrating specificity of ImmTAC molecules of FIG. 5, comprising the mutated PRAME TCR variable domains as set out in FIGS. 3 and 4.

The data presented in FIG. 7 (panel a) demonstrate that ImmTAC molecules comprising mutated alpha and beta chain a28b50 and a79b46 show minimal reactivity against a panel of 8 normal cells relative to antigen positive cancer cells at a concentration up to 1 nM. Likewise, the data in FIG. 7 (panel b) demonstrate that ImmTAC molecules comprising a28b57 and a79b46 show minimal reactivity against a panel of 4 normal cells relative to antigen positive cancer cells at a concentration up to 1 nM.

Example 8—Cancer Cell Killing Mediated by Certain Mutated TCRs of the Invention

The ability of ImmTAC molecules comprising the mutated TCR sequences to mediate potent redirected T cell killing of antigen positive tumour cells was investigated using the IncuCyte platform (Essen BioScience). This assay allows real time detection by microscopy of the release of Caspase-3/7, a marker for apoptosis.

Method

Assays were performed using the CellPlayer 96-well Caspase-3/7 apoptosis assay kit (Essen BioScience, Cat. No. 4440) and carried out according the manufacturers protocol. Briefly, target cells (Me1624 (PRAME+ve HLA-A*02+ve)

or NCI-H1755) were plated at 10,000 cells per well and incubated overnight to allow them to adhere. ImmTAC molecules were prepared at various concentrations and 25 µl of each was added to the relevant well such that final concentrations were between 1 µM and 100 µM. Effector cells were used at an effector target cell ratio of 10:1 (100,000 cells per well). A control sample without ImmTAC was also prepared along with samples containing either effector cells alone, or target cells alone. NucView assay reagent was made up at 30 µM and 25 µl added to every well and the final volume brought to 150 µl (giving 5 µM final conc). The plate was placed in the IncuCyte instrument and images taken every 2 hours (1 image per well) over 3 days. The number of apoptotic cells in each image was determined and recorded as apoptotic cells per mm². Assays were performed in triplicate.

The data presented in this example includes ImmTAC molecules comprising the following TCR alpha and beta chains
a28b50
a79b74
a79b46

The full amino acid sequences of ImmTAC molecules comprising a28b50, a79b74 and a79b46 are provided in FIG. 5 (ImmTAC 1, 2 and 3 respectively).

Results

The data presented in FIGS. 8 and 9 shows real-time killing of antigen positive cancer cells (Melanoma cell lines Me1624 in FIG. 8 and Lung cancer cell line NCI-H1755 in FIG. 9) in the presence of ImmTAC molecules comprising the mutated TCR sequences, at a concentration of 100 µM or lower. No killing was observed in the absence of ImmTAC molecules.

What is claimed is:

1. A heterodimeric TCR-anti-CD3 antibody fusion molecule, comprising a first polypeptide chain that comprises a TCR alpha chain variable domain and a second polypeptide chain that comprises a TCR beta chain variable domain, wherein:

the alpha chain variable domain has the amino acid sequence set forth in SEQ ID NO: 6 and the beta chain variable domain has the amino acid sequence set forth in SEQ ID NO:
9;

the alpha chain variable domain has the amino acid sequence set forth in SEQ ID NO: 7 and the beta chain variable domain has the amino acid sequence set forth in SEQ ID NO:
11;

the alpha chain variable domain has the amino acid sequence set forth in SEQ ID NO: 7 and the beta chain variable domain has the amino acid sequence set forth in SEQ ID NO: 17; or the alpha chain variable domain has the amino acid sequence set forth in SEQ ID NO: 7 and the beta chain variable domain has the amino acid sequence set forth in SEQ ID NO:
18.

2. The heterodimeric TCR-anti-CD3 antibody fusion molecule of claim 1, wherein the alpha chain variable domain has the amino acid sequence set forth in SEQ ID NO: 6 and the beta chain variable domain has the amino acid sequence set forth in SEQ ID NO: 9.

3. The heterodimeric TCR-anti-CD3 antibody fusion molecule of claim 1, wherein the alpha chain variable domain has the amino acid sequence set forth in SEQ ID NO: 7 and the beta chain variable domain has the amino acid sequence set forth in SEQ ID NO: 11.

4. The heterodimeric TCR-anti-CD3 antibody fusion molecule of claim 1, wherein the alpha chain variable domain has the amino acid sequence set forth in SEQ ID NO: 7 and the beta chain variable domain has the amino acid sequence set forth in SEQ ID NO: 17.

5. The heterodimeric TCR-anti-CD3 antibody fusion molecule of claim 1, wherein the alpha chain variable domain has the amino acid sequence set forth in SEQ ID NO: 7 and the beta chain variable domain has the amino acid sequence set forth in SEQ ID NO: 18.

6. The heterodimeric TCR-anti-CD3 antibody fusion molecule of claim 1, wherein the TCR has a single chain format of the type Vα-L-Vβ, Vβ-L-Vα, Vα-Cα-L-Vβ, or Vα-L-Vβ-Cβ, wherein Vα and Vβ are TCR α and β variable regions respectively, Cα and Cβ are TCR α and β constant regions respectively, and L is a linker sequence.

7. The heterodimeric TCR-anti-CD3 antibody fusion molecule of claim 1, wherein the TCR comprises an alpha chain TRAC constant domain sequence and a beta chain TRBC1 or TRBC2 constant domain sequence.

8. The heterodimeric TCR-anti-CD3 antibody fusion molecule of claim 7, wherein the alpha chain constant domain sequence and the beta chain constant domain sequence are modified by truncation or amino acid substitution to delete a native disulfide bond between Cys4 of exon 2 of TRAC and Cys2 of exon 2 of TRBC1 or TRBC2.

9. The heterodimeric TCR-anti-CD3 antibody fusion molecule of claim 7, wherein the alpha chain constant domain sequence is modified by substitution of a cysteine residue for Thr 48 of TRAC and the beta chain constant domain sequence is modified by substitution of a cysteine residue for Ser 57 of TRBC1 or TRBC2, wherein the cysteine residues form a non-native disulfide bond between the alpha constant domain and the beta constant domain of the TCR.

10. The heterodimeric TCR-anti-CD3 antibody fusion molecule of claim 1, wherein the anti-CD3 antibody is a Fab fragment, F(ab')$_2$ fragment, dsFv fragment, scFv fragment, minibody, nanobody, or domain antibody.

11. The heterodimeric TCR-anti-CD3 antibody fusion molecule of claim 10, wherein the anti-CD3 antibody is an scFv having the amino acid sequence of residues 1-253 of SEQ ID NO: 26, residues 1-253 of SEQ ID NO: 28, or residues 1-253 of SEQ ID NO: 30.

12. The heterodimeric TCR-anti-CD3 antibody fusion molecule of claim 11, wherein the anti-CD3 antibody is an scFv having the amino acid sequence of residues 1-253 of SEQ ID NO: 26.

13. The heterodimeric TCR-anti-CD3 antibody fusion molecule of claim 11, wherein the anti-CD3 antibody is an scFv having the amino acid sequence of residues 1-253 of SEQ ID NO: 28.

14. The heterodimeric TCR-anti-CD3 antibody fusion molecule of claim 11, wherein the anti-CD3 antibody is an scFv having the amino acid sequence of residues 1-253 of SEQ ID NO: 30.

15. The heterodimeric TCR-anti-CD3 antibody fusion molecule of claim 11, wherein the scFv is covalently linked to the N-terminus of the beta chain variable domain via a linker sequence.

16. The heterodimeric TCR-anti-CD3 antibody fusion molecule of claim 15, wherein the linker sequence is selected from the group consisting of: GGGGS (SEQ ID NO: 31), GGGSG (SEQ ID NO: 32), GGSGG (SEQ ID NO: 33), GSGGG (SEQ ID NO: 34), GSGGGP (SEQ ID NO: 35), GGEPS (SEQ ID NO: 36), GGEGGGP (SEQ ID NO: 37), and GGEGGGSEGGGS (SEQ ID NO: 38).

17. The heterodimeric TCR-anti-CD3 antibody fusion molecule of claim 16, wherein the linker sequence is GGGGS (SEQ ID NO: 31).

18. A pharmaceutical composition comprising the heterodimeric TCR-anti-CD3 antibody fusion molecule of claim 1, together with one or more pharmaceutically acceptable carriers or excipients.

19. A method of treating a human subject having cancer, comprising:
administering to the subject a therapeutically effective dose of the pharmaceutical composition of claim 18.

20. The method of claim 19, wherein the cancer expresses the antigen PRAME.

21. The method of claim 20, wherein the cancer is selected from melanoma, lung cancer, breast cancer, ovarian cancer, endometrial cancer, esophageal cancer, bladder cancer, and head and neck cancer.

22. The method of claim 19, wherein the pharmaceutical composition is administered by injection.

\* \* \* \* \*